(12) United States Patent
Furukawa et al.

(10) Patent No.: US 10,874,604 B2
(45) Date of Patent: *Dec. 29, 2020

(54) COSMETIC COMPOSITION OR EXTERNAL COMPOSITION, AND COSMETIC RAW MATERIAL COMPOSITION

(71) Applicants: DOW TORAY CO., LTD., Tokyo (JP); DOW SILICONES CORPORATION, Midland, MI (US)

(72) Inventors: Haruhiko Furukawa, Ichihara (JP); John Bernard Horstman, Midland, MI (US); Tomohiro Iimura, Ichihara (JP); Tadashi Okawa, Ichihara (JP); Steven Swier, Midland, MI (US)

(73) Assignees: DOW TORAY CO., LTD., Tokyo (JP); DOW SILICONES CORPORATION, Midland, MI (US)

(*) Notice: Subject to any disclaimer, the term of this patent is extended or adjusted under 35 U.S.C. 154(b) by 54 days.

This patent is subject to a terminal disclaimer.

(21) Appl. No.: 16/339,292

(22) PCT Filed: Oct. 3, 2017

(86) PCT No.: PCT/JP2017/035985
§ 371 (c)(1),
(2) Date: Apr. 3, 2019

(87) PCT Pub. No.: WO2018/066559
PCT Pub. Date: Apr. 12, 2018

(65) Prior Publication Data
US 2020/0038312 A1    Feb. 6, 2020

Related U.S. Application Data

(60) Provisional application No. 62/403,951, filed on Oct. 4, 2016, provisional application No. 62/403,955, filed on Oct. 4, 2016.

(51) Int. Cl.
| | |
|---|---|
| A61K 8/891 | (2006.01) |
| A61Q 19/00 | (2006.01) |
| A61K 8/894 | (2006.01) |
| C08L 83/10 | (2006.01) |
| A61K 8/06 | (2006.01) |
| A61K 8/34 | (2006.01) |
| A61K 8/90 | (2006.01) |
| A61Q 1/02 | (2006.01) |
| A61Q 17/04 | (2006.01) |
| C08G 77/42 | (2006.01) |

(Continued)

(52) U.S. Cl.
CPC .............. *A61K 8/891* (2013.01); *A61K 8/062* (2013.01); *A61K 8/064* (2013.01); *A61K 8/34* (2013.01); *A61K 8/894* (2013.01); *A61K 8/90* (2013.01); *A61Q 1/02* (2013.01); *A61Q 19/00* (2013.01); *C08L 83/10* (2013.01); *A61K 2800/10* (2013.01); *A61Q 17/04* (2013.01); *C08G 77/16* (2013.01); *C08G 77/42* (2013.01); *C08G 77/46* (2013.01)

(58) Field of Classification Search
None
See application file for complete search history.

(56) References Cited

U.S. PATENT DOCUMENTS 2,736,721 A * 2/1956 Dexter .................... C08L 83/00
  525/475
2,814,601 A * 11/1957 Currie ........................ C09J 7/21
  528/18

(Continued)

FOREIGN PATENT DOCUMENTS

| JP | H02137737 A | 5/1990 |
| JP | H08143426 A | 6/1996 |

(Continued)

OTHER PUBLICATIONS

English translation of International Search Report for International Application No. PCT/JP2017/036021 dated Dec. 5, 2017, 1 page.

(Continued)

*Primary Examiner* — Peter A Salamon
(74) *Attorney, Agent, or Firm* — Warner Norcross + Judd LLP

(57) ABSTRACT

A cosmetic composition and a topical composition containing a resin-linear organopolysiloxane block copolymer are provided, which are excellent in compatibility with other cosmetic raw materials, so as to have a high degree of freedom in formulation design, excellent film forming properties and film following properties, and suppressed tackiness of the film. The resin-linear organopolysiloxane block copolymer contains a resin-linear organopolysiloxane block copolymer (A) having a structure in which a resin structure (A1) block having a siloxane unit represented by $R^1SiO_{3/2}$ (where $R^1$ is a monovalent organic group, a hydroxyl group, or an alkoxy group having 1 to 6 carbon atoms) or by $SiO_{4/2}$ and a linear structure (A2) block represented by $(R_2SiO_{2/2})_n$ (where n is a number of 5 or more, R is an alkyl group, a fluoroalkyl group, or an aryl group) are connected by a Si—O—Si bond and has an $R^1SiO_{3/2}$ unit.

14 Claims, No Drawings

(51) Int. Cl.
*C08G 77/46* (2006.01)
*C08G 77/16* (2006.01)

(56) References Cited

U.S. PATENT DOCUMENTS

| | | | | |
|---|---|---|---|---|
| 5,160,730 | A * | 11/1992 | Dubief | A61K 8/585 424/59 |
| 6,337,086 | B1 * | 1/2002 | Kanios | A61K 9/7061 424/448 |
| 7,261,877 | B2 | 8/2007 | Luo et al. | |
| 9,705,056 | B2 * | 7/2017 | Amako | H01L 33/58 |
| 9,927,703 | B2 * | 3/2018 | Swier | G03F 7/0007 |
| 2003/0091523 | A1 * | 5/2003 | Dhamdhere | A61K 8/892 424/70.12 |
| 2006/0280693 | A1 * | 12/2006 | Ivanova | A61Q 5/12 424/47 |
| 2007/0196309 | A1 * | 8/2007 | Tarletsky | C08L 83/14 424/70.12 |
| 2010/0215595 | A1 | 8/2010 | Kennan et al. | |
| 2010/0284941 | A1 * | 11/2010 | Ivanova | A61K 8/046 424/47 |
| 2011/0097579 | A1 * | 4/2011 | Mizuno | C09J 183/04 428/355 R |
| 2012/0046486 | A1 | 2/2012 | Henning et al. | |
| 2013/0165602 | A1 * | 6/2013 | Horstman | C08G 77/16 525/477 |
| 2013/0168727 | A1 * | 7/2013 | Horstman | C09D 183/10 257/100 |
| 2013/0172496 | A1 * | 7/2013 | Horstman | C08G 77/44 525/477 |
| 2013/0245187 | A1 * | 9/2013 | Swier | C08G 77/14 524/500 |
| 2014/0031465 | A1 * | 1/2014 | Horstman | C08G 77/44 524/158 |
| 2014/0161756 | A1 * | 6/2014 | Beer | A61Q 5/12 424/70.122 |
| 2014/0357773 | A1 * | 12/2014 | Liles | C09J 183/06 524/377 |
| 2014/0357827 | A1 * | 12/2014 | Swier | C08L 83/10 528/10 |
| 2014/0371317 | A1 * | 12/2014 | Aliyar | C08L 83/04 514/567 |
| 2015/0001567 | A1 * | 1/2015 | Amako | H01L 33/56 257/98 |
| 2015/0031826 | A1 * | 1/2015 | Horstman | C08L 83/10 524/588 |
| 2015/0031841 | A1 * | 1/2015 | Horstman | H01L 23/296 525/477 |
| 2015/0051356 | A1 * | 2/2015 | Colas | C08G 77/42 525/478 |
| 2015/0073077 | A1 * | 3/2015 | Horstman | C08G 77/70 524/268 |
| 2015/0087771 | A1 * | 3/2015 | Horstman | C08G 77/42 524/588 |
| 2015/0087772 | A1 * | 3/2015 | Horstman | C09D 183/10 524/588 |
| 2015/0112011 | A1 * | 4/2015 | Swier | C09D 183/10 524/430 |
| 2015/0207047 | A1 * | 7/2015 | Amako | H01L 33/56 257/98 |
| 2015/0340839 | A1 | 11/2015 | Zhang et al. | |
| 2016/0009866 | A1 * | 1/2016 | Swier | H01L 51/5237 528/43 |
| 2016/0118555 | A1 * | 4/2016 | Swier | C09D 183/10 524/113 |
| 2016/0204319 | A1 * | 7/2016 | Swier | B32B 27/06 428/339 |
| 2016/0208055 | A1 * | 7/2016 | Horstman | C08G 77/20 |
| 2017/0152411 | A1 * | 6/2017 | Mihara | C09J 7/10 |
| 2017/0194539 | A1 * | 7/2017 | Henning | B32B 27/283 |
| 2020/0038312 | A1 * | 2/2020 | Furukawa | A61Q 1/02 |

FOREIGN PATENT DOCUMENTS

| | | |
|---|---|---|
| JP | 2006504603 A | 2/2006 |
| JP | 2010065221 A | 3/2010 |
| JP | 2010540727 A | 12/2010 |
| JP | 2012184353 A | 9/2012 |
| WO | 0007550 A1 | 2/2000 |
| WO | 2004037941 A2 | 5/2004 |
| WO | 2004084847 A1 | 10/2004 |
| WO | 2005063890 A2 | 7/2005 |
| WO | 2012040367 A1 | 3/2012 |
| WO | 2012106391 A1 | 8/2012 |
| WO | 2013142138 A1 | 9/2013 |
| WO | 2014040367 A1 | 3/2014 |
| WO | 2014151464 A1 | 9/2014 |
| WO | 2014151587 A2 | 9/2014 |
| WO | 2014152522 A1 | 9/2014 |
| WO | 2015042285 A1 | 3/2015 |
| WO | 2016031551 A1 | 3/2016 |

OTHER PUBLICATIONS

English translation of International Search Report for International Application No. PCT/JP2017/035985 dated Dec. 19, 2017, 1 page.
Machine assisted translation of JPH02137737A obtained from https://worldwide.espacenet.com on Mar. 29, 2019, 13 pages.
Machine assisted translation of JPH08143426A obtained from https://worldwide.espacenet.com on Apr. 2, 2019, 11 pages.
Machine assisted translation of JP2012184353A obtained from https://worldwide.espacenet.com on Mar. 29, 2019, 33 pages.

* cited by examiner

COSMETIC COMPOSITION OR EXTERNAL COMPOSITION, AND COSMETIC RAW MATERIAL COMPOSITION

CROSS-REFERENCE TO RELATED APPLICATIONS

This application is the National Stage of International Application No. PCT/JP2017/035985 filed on 3 Oct. 2017, which claims priority to and all advantages of U.S. Provisional Appl. Nos. 62/403,951 and 62/403,955 filed on 4 Oct. 2016, the contents of which is hereby incorporated by reference.

TECHNICAL FIELD

The present invention relates to cosmetic compositions or preparations for external use, and cosmetic raw material compositions containing resin-linear organopolysiloxane block copolymers.

BACKGROUND ART

Resin-linear organopolysiloxane block copolymers having a resin structure consisting of branched siloxane units and a linear (chain) structure consisting of disiloxane units in the same molecule are used in various applications because they have unique physical properties such as a film-forming property derived from a resin structure, and film followability and flexibility derived from a linear structure, as well as excellent curing properties and film-forming properties, unlike organopolysiloxane having a resin or linear structure only. Examples of such a resin-linear organopolysiloxane block copolymer include a condensation reaction product of an organopolysiloxane having a resin structure and an organopolysiloxane having a linear structure, and the like.

For example, Patent Documents 1 to 4 disclose a condensation reaction product of an organopolysiloxane having a linear structure mainly having an MQ type organopolysiloxane resin and a D unit, and a cosmetic composition containing an MDQ type organopolysiloxane. While these cosmetic compositions can be expected to improve film-forming properties and feel derived from an organopolysiloxane condensation reaction product, particularly when an organopolysiloxane condensation reaction product is blended in large quantities, compatibility with other oleophilic cosmetic raw materials may become insufficient, which may cause deterioration in feel such as precipitation of the condensation reaction product. Therefore, the conventional organopolysiloxane condensation reaction products have a low degree of freedom in formulation design, and it has been difficult to fully utilize the advantages such as film-forming property based on the provision of both resin and linear structures. In addition, conventional organopolysiloxane condensation reaction products, particularly when blended in cosmetics, can stand further improvement in feel, such as the tackiness of a film derived from a resin structure.

PRIOR ART DOCUMENTS

Patent Documents

[Patent Document 1] US 2007/0196309 A
[Patent Document 2] WO 2014/151464
[Patent Document 3] U.S. Pat. No. 7,261,877
[Patent Document 4] JP 08-143426 A

SUMMARY OF THE INVENTION

Problems to be Solved by the Invention

It is an object of the present invention to provide a cosmetic composition or a preparation for external use, which contains a resin-linear organopolysiloxane block copolymer, the composition or the preparation having a high degree of freedom of formulation design for sake of excellent compatibility with other cosmetic raw materials, excellent film-forming properties and film followability, and suppressed tackiness of the film, etc. It is a further object of the present invention to provide a cosmetic raw material containing a resin-linear organopolysiloxane block copolymer having the above advantages.

Means for Solving the Problems

A cosmetic composition or a preparation for external use of the present invention is characterized by including a resin-linear organopolysiloxane block copolymer (A) having a structure in which a resin structure (A1) represented by $R^1SiO_{3/2}$ ($R^1$ is a monovalent organic group, a hydroxyl group, or an alkoxy group having 1 to 6 carbon atoms) or by $SiO_{4/2}$ and a linear structure (A2) represented by $(R_2SiO_{2/2})_n$ (n is a number of 5 or more, R is an alkyl group, a fluoroalkyl group, or an aryl group) are connected by a Si—O—Si bond in the molecule, and by having $R^1SiO_{3/2}$ units in the molecule.

In the Si—O—Si bond connecting the resin structure (A1) and the linear structure (A2) in the resin-linear organopolysiloxane block copolymer (A) described above, it is preferred that the Si atom bonded to the resin structure (A1) constitutes $RSiO_{3/2}$ units.

It is preferable that the resin-linear organopolysiloxane block copolymer (A) contains $PhSiO_{3/2}$ (Ph is a phenyl group) units or $R^2SiO_{3/2}$ ($R^2$ is an alkyl group having 3 to 20 carbon atoms) units. In particular, it is preferable that the resin-linear organopolysiloxane block copolymer (A) contains $R^4R^5R^6SiO_{1/2}$ ($R^4$ to $R^6$ are each independently monovalent organic groups and at least two of them are aryl groups) units.

Further, the resin-linear organopolysiloxane block copolymer (A) preferably has a hydroxyl group (OH) content in the molecule of 1.50 mass % or more, more preferably 2.00 mass % or more.

The cosmetic composition or the preparation for external use of the present invention preferably contains a solvent (B) of the resin-linear organopolysiloxane block copolymer (A). Further, from the viewpoint of compatibility with other cosmetic raw materials, it is preferable that the resin-linear organopolysiloxane block copolymer (A) and the solvent (B) thereof have solubility in cinnamic acid methyl ester.

In the cosmetic composition or the preparation for external use of the present invention, it is preferable that the solvent (B) is a volatile solvent (B1).

The cosmetic composition or the preparation for external use of the present invention preferably further contains an oleophilic cosmetic raw material (C), a surfactant (D), a powder (E) or alcohols (F).

The cosmetic composition or the preparation for external use of the present invention is preferably in a form of an oil-in-water emulsion or a water-in-oil emulsion.

The cosmetic raw material composition of the present invention contains a resin-linear organopolysiloxane block copolymer (A) having a structure in which a resin structure (A1) represented by $R^1SiO_{3/2}$ ($R^1$ is a monovalent organic group, a hydroxyl group, or an alkoxy group having 1 to 6 carbon atoms) or by $SiO_{4/2}$ and a linear structure (A2) represented by $(R_2SiO_{2/2})_n$ (n is a number of 5 or more) are connected by a Si—O—Si bond, and further having $R^1SiO_{3/2}$ units and a volatile solvent (B1), and a suitable resin-linear organopolysiloxane block copolymer (A) is the same as described above.

Effects of the Invention

According to the present invention, it is possible to provide a cosmetic composition or a preparation for external use containing a resin-linear organopolysiloxane block copolymer, the composition or the preparation having a high degree of freedom of formulation design for sake of excellent compatibility with other cosmetic raw materials, excellent film-forming properties and film followability, and suppressed tackiness of the film, etc. In addition, the present invention can provide a cosmetic raw material containing a resin-linear organopolysiloxane block copolymer having the above advantages.

MODE FOR CARRYING OUT THE INVENTION

[Resin-Linear Organopolysiloxane Block Copolymer (A)]

The cosmetic composition or the preparation for external use of the present invention is characterized by including a resin-linear organopolysiloxane block copolymer (A) having a structure in which a resin structure (A1) block that has siloxane units represented by $R^1SiO_{3/2}$ ($R^1$ is a monovalent organic group, a hydroxyl group, or an alkoxy group having 1 to 6 carbon atoms) or by $SiO_{4/2}$ and a linear structure (A2) block represented by $(R_2SiO_{2/2})_n$ (n is a number of 5 or more, R is an alkyl group, a fluoroalkyl group, or an aryl group) are connected by a Si—O—Si bond in the molecule, and by having $R^1SiO_{3/2}$ units in the molecule. Here, the $R^1SiO_{3/2}$ units are essential constituent units of the polymer (A), and in particular, it is preferable that, in the Si—O—Si bond connecting the resin configuration (A1) block and the linear structure (A2) block in the polymer (A), the Si atom bonded to the resin structure (A1) constitutes $R^1SiO_{3/2}$ units. Hereinafter, the resin-linear organopolysiloxane block copolymer (A) may be simply referred to as "copolymer (A)" when the component is described.

The copolymer (A) has a resin structure (A1) block and a linear structure (A2) block. The resin structure (A1) block is a resinous (resin) organopolysiloxane structure that contains T units or Q units represented by $R^1SiO_{3/2}$ ($R^1$ is a monovalent organic group, a hydroxyl group, or an alkoxy group having 1 to 6 carbon atoms) or by $SiO_{4/2}$ as essential siloxane units and forms partial structures consisting of resinous organopolysiloxanes in which a large number of T units or Q units are bonded. Such a resin structure is a partial structure which imparts a film-forming property when the copolymer (A) of the present invention is incorporated into a cosmetic composition or a preparation for external use.

Examples of such resin structures (A1) include an MQ resin, an MDQ resin, an MTQ resin, an MDTQ resin, an MT resin, a T resin, a TD resin, a TQ resin, and a TDQ resin, which are consisted of any combinations including a triorganosiloxy unit (M unit) represented by $R^1_3SiO_{1/2}$ ($R^1$ is a monovalent organic group, a hydroxyl group, or an alkoxy group having 1 to 6 carbon atoms), and a diorganosiloxy unit (D unit) represented by $R^1_2SiO_{2/2}$ ($R^1$ is a monovalent organic group, a hydroxyl group, or an alkoxy group having 1 to 6 carbon atoms), in addition to the above-mentioned T unit or Q unit. In particular, an MQ resin, an MT resin, or a T resin is preferable. However, in relation to the linear structure (A2) described later, the resin structure (A1) does not include a partial structure in which 5 or more D units are consecutively included.

The functional groups $R^1$ on the siloxane unit constituting the resin structures (A1) are each independently a monovalent organic group, a hydroxyl group, or an alkoxy group having 1 to 6 carbon atoms. In particular, the functional groups $R^1$ include an alkyl group having 1 to 20 carbon atoms, a halogen-substituted alkyl group having 1 to 20 carbon atoms, an aryl group having 6 to 20 carbon atoms, a halogen-substituted aryl group having 6 to 20 carbon atoms, an aralkyl group having 7 to 20 carbon atoms, an alkenyl group having 2 to 20 carbon atoms, an acryl-containing group, a methacryl-containing group, an alkoxy group having 1 to 6 carbon atoms, and a hydroxyl group.

Specifically, the functional groups $R^1$ include alkyl groups such as a methyl group, an ethyl group, a propyl group, a butyl group, a pentyl group, a hexyl group, a heptyl group, an octyl group, a nonyl group, a decyl group, an undecyl group and a dodecyl group; aryl groups such as a phenyl group, a tolyl group, a xylyl group, a naphthyl group, an anthracenyl group, a phenanthryl group and a pyrenyl group; aralkyl groups such as a phenethyl group and a phenylpropyl group; and groups in which some or all of the hydrogen atoms bonded to these groups are substituted with a halogen atom such as a fluorine atom, a chlorine atom, a bromine atom or the like; alkoxy groups such as a methoxy group, an ethoxy group or a propoxy group; alkenyl groups having 2 to 20 carbon atoms such as a vinyl group, an allyl group, a butenyl group, a pentenyl group, a hexenyl group, a heptenyl group, an octenyl group, a nonenyl group, a decenyl group, an undecenyl group, a dodecenyl group; acrylic-containing groups such as a 3-acryloxypropyl group, a 4-acryloxybutyl group; methacryl-containing groups such as a 3-methacryloxypropyl group, a 4-methacryloxybutyl group; and hydroxyl groups.

From an industrial point of view, the functional group $R^1$ on the siloxane unit constituting the resin structure (A1) is preferably an alkyl group, a fluorine-substituted alkyl group, an aryl group, an alkenyl group, an alkoxy group or a hydroxyl group, and is preferably a group selected from a methyl group, an ethyl group, a propyl group, a phenyl group, a vinyl group, a hexenyl group, a methoxy group, an ethoxy group and a hydroxyl group. In particular, when a large number of aryl groups such as phenyl groups are contained in the molecule, the refractive index of the polymer (A) is improved, and a highly transparent appearance is provided at the time of film-forming, which is particularly preferable.

The organopolysiloxane resin raw material providing the resin structure (A1) block of the copolymer (A) preferably has a weight-average molecular weight in the range of 500 to 20,000, more preferably in the range of 1,000 to 15,000, and more preferably in the range of 1,500 to 12,000. The organopolysiloxane resin raw material providing the resin structure (A1) block may be two or more kinds having different weight-average molecular weights, hydroxyl group contents, ratios of siloxane units (M, D, T, Q units), and the like. The weight-average molecular weight (weight-average molecular weight based on styrene polymer) of the resin structure (A1) block in the molecule of the copolymer (A) varies depending on the organopolysiloxane resin as a raw material and the degree of condensation reaction between the hydroxyl groups in the organopolysiloxane resin.

The linear structure (A2) is a non-reactive block represented by $(R_2SiO_{2/2})_n$ (n is a number of 5 or more, R is an alkyl group, a fluoroalkyl group or an aryl group), and has a structure in which diorganosiloxy units represented by $R_2SiO_{2/2}$ are connected in a chain form by at least 5 units or more. Such a linear structural (A2) block is a partial structure that gives flexibility and followability to the film formed by the copolymer (A). In the formula, n is the degree of polymerization of the diorganosiloxy unit constituting the partial structure, preferably in the range of 5 to 1000, more preferably in the range of 5 to 500, 10 to 300, and 15 to 200. When n in the partial structure exceeds the above upper limit, the property as a linear molecule derived from the linear structure is strongly expressed, and the film-forming property or the like may be deteriorated in some cases. On the other hand, when n is less than the above-mentioned lower limit, the property as a linear molecule is not sufficient, and the characteristic physical property of the copolymer (A) cannot be realized in some cases.

The functional group R on the diorganosiloxy unit constituting the linear structure (A2) is an alkyl group, a fluoroalkyl group or an aryl group, which is unreactive with respect to the resin structure (A1) and the functional group in the same molecule, and it is necessary to maintain the linear structure (A2) without causing a polymerization reaction such as a condensation reaction within the molecule. The alkyl group and the aryl group are the same groups as described above, and a methyl group or a phenyl group is preferable from an industrial point of view.

The diorganopolysiloxane providing the linear structure (A2) block of the copolymer (A) is a chain organopolysiloxane in which the degree of polymerization of the diorganosiloxy unit having a hydroxyl group or a hydrolyzable functional group at the molecular chain end is in the above range (such as in the range of 5 to 1000), and is preferably a diorganopolysiloxane in which the degree of polymerization of the diorganosiloxy unit is 15 to 200 and the hydroxyl group (silanol group) at the molecular chain end or a disiloxysilyl end, a dioximesilyl end or a dialkoxy silyl end derived from the silanol group described later.

[Resin/Linear Structure Connecting Portion of the Copolymer (A)]

The copolymer (A) is characterized by having a structure in which the resin structure (A1) and the linear structure (A2) are connected by a Si—O—Si bond, and having $R^1SiO_{3/2}$ units. A plurality of partial structures connected by these Si—O—Si bonds may be included in the molecules, and it is preferable that each partial structure has $R^1SiO_{3/2}$ units. The functional group $R^1$ is the same group as above, and preferably a group selected from a methyl group, an ethyl group, a propyl group, a phenyl group, a vinyl group, a hexenyl group, a methoxy group, an ethoxy group, and a hydroxyl group. The Si—O—Si bonds connecting the structures are siloxane bonds between silicon atoms constituting the resin structure (A1) or the linear structure (A2), the silicon atoms on the T unit or the Q unit represented by $R^1SiO_{3/2}$ or $SiO_{4/2}$ constituting the resin structure (A1) respectively, and the silicon atoms of the linear structure (A2) represented by $(R_2SiO_{2/2})_n$ (n is a number of 5 or more, and R is an alkyl group, a fluoroalkyl group or an aryl group) form a partial structure (T-Dn) or (Q-Dn) as follows. In the present invention, it is particularly preferred that the Si atoms bonded to the resin structure (A1) constitute $RSiO_{3/2}$ units, and it is particularly preferred that the Si atoms have the following partial structure (T-Dn).

Partial structure (T-Dn)

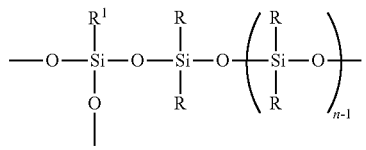

[Formula 1]

(T-Dn)

Partial structure (Q-Dn)

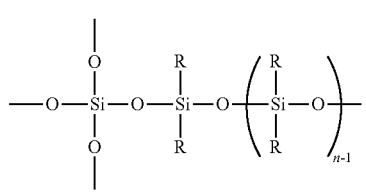

[Formula 2]

(Q-Dn)

In the above partial structure, the end of the left Si—O-bond constituting the T unit or the Q unit is bonded to a hydrogen atom or another siloxane unit constituting the resin structure (A1), respectively. However, at least one of Si—O-bonds is bonded to another siloxane unit constituting the resin structure (A1). On the other hand, the end of the right Si—O-bond are bonded to other siloxane unit, triorganosiloxy unit (M unit) or a hydrogen atom that forms a linear structure (A2) or a resin structure (A1). It is needless to say that a silanol group (Si—OH) is formed when a hydrogen atom is bonded to the end of the Si—O-bond.

The above partial structures need to be at least one in the molecule, but may have two or more of the above partial structures in the molecule. Particularly preferred is a resin-linear organopolysiloxane block copolymer having at least one of the partial structures (T-Dn) in the molecule thereof from the viewpoint of compatibility and affinity with cosmetic raw materials.

Such partial structures (T-Dn) may suitably be constituted by condensation reacting an organopolysiloxane having a linear structure with a diacyloxysilyl end, a dioxime silyl end or a dialkoxysilyl end with an organopolysiloxane having a resin structure. More specifically, the partial structure (T-Dn) can be obtained by a manufacturing method of a resin-linear organopolysiloxane block copolymer having steps of: (I) condensation reaction of an organopolysiloxane with a linear structure having a silanol end (—OH) with a triacyloxysilane to form an organopolysiloxane having a linear structure with a diacyloxysilyl end, a dioxime silyl end or a dialkoxysilyl end; and (II) following step (I), condensation reaction of the organopolysiloxane having a linear structure with a diacyloxysilyl end, a dioxime silyl end or a dialkoxysilyl end with an organopolysiloxane having a hydroxyl group and a resin structure in the molecule to obtain a resin-linear organopolysiloxane block copolymer having a Si—O—Si bond between the linear structure and the resin structure, and the Si atom bonded to the resin structure constitutes the $RSiO_{3/2}$ unit.

In step (I) above, since the $RSiO_{3/2}$ units of the connecting moiety are derived from triacyloxysilane, trioxymylane or trialkoxysilane, the functional groups on the $RSiO_{3/2}$ units bonded to the resin structures (A1) in the polymer can be designed by selecting triacyloxysilane, trioxymylane or trialkoxysilane having particular functional groups. Specifically, the functional group R bonded to silicon atoms constituting an organotriacetoxysilane represented by R(CH3COO)3Si is introduced on the $RSiO_{3/2}$ units of the connecting portion. Therefore, by using phenyltriacetoxysilane represented by (Ph)(CH3COO)3Si or alkyltriacetoxysilane represented by $R^2$(CH3COO)3Si ($R^2$ is an alkyl group having 3 to 20 carbon atoms), a resin-linear organopolysiloxane block copolymer containing a $PhSiO_{3/2}$ (Ph is a phenyl group) unit or an $R^2Si_{3/2}$ ($R^2$ is an alkyl group having 3 to 20 carbon atoms) unit can be easily obtained.

The copolymer (A) may have an aryl group such as a phenyl group in the molecule, and in particular, a triorganosiloxy group constituting an end of a resin structure or a linear structure may have at least one or more aryl groups. The high content of aryl groups in the copolymer (A) of the present invention tends to increase the refractive index of the polymer as a whole, and the optical transparency may be improved.

The copolymer (A) may further have one or more functional groups selected from an alkyl group having 6 or more carbon atoms, a fluoroalkyl group, a Si-macromonomer, and a Si-dendrimer modifying group in the molecule. Since these functional groups have from high hydrophobicity to water repellency, and affinity for specific components, the film formed by the copolymer (A) may be further improved in functionality in some cases.

The copolymer (A) may have a triorganosiloxy group having at least two aryl groups in the molecule, and may contain $R^4R^5R^6SiO_{1/2}$ units ($R^4$ to $R^6$ are each independently a monovalent organic group, at least two of them are aryl groups). Such triorganosiloxy groups may be triorganosiloxy groups having at least two phenyl groups or triorganosiloxy groups having three phenyl groups. Also, a triorganosiloxy group having at least two aryl groups other than phenyl groups may be used. Such triorganosiloxy group is introduced by condensation reactions using an organosilane represented by $R^4R^5R^6SiX$ ($R^4$ to $R^6$ are each independently a monovalent organic groups, at least two of them are aryl groups, and X is a hydroxyl group or a hydrolyzable group) as a raw material.

[Hydroxyl Group Content of Copolymer (A)]

From the viewpoint of compatibility and affinity with other cosmetic raw materials, the copolymer (A) preferably has a hydroxyl group in the molecule, preferably has a hydroxyl group (OH) content in the molecule of 1.50 mass % or more, more preferably 1.75 mass % or more, more preferably 2.0 mass % or more, and particularly preferably 2.25 mass % or more. Most preferably, the hydroxyl group (OH) content of the copolymer is in the range of 2.25 to 3.50 mass %. The copolymer may be a single type or a mixture of copolymers having two different hydroxyl group (OH) contents, but the average value of the hydroxyl group (OH) contents of these copolymers is preferably in the above range.

In particular, the copolymer (A) can preferably be obtained by condensation reaction of an organopolysiloxane having a linear structure with a diacyloxysilyl end, a dioxime silyl end or a dialkoxysilyl end and an organopolysiloxane having a resin structure. Since the reaction by the disiloxysilyl end, the dioximesilyl end or the dialkoxysilyl end proceeds selectively with respect to the hydroxyl group on the organopolysiloxane having the resin structure, many hydroxyl groups react between the organopolysiloxanes having the resin structure and it is possible to synthesize a resin-linear organopolysiloxane block copolymer in which a competitive reaction in which the hydroxyl group (OH) content of the copolymer is lowered hardly occurs and a large number of hydroxyl groups (OH) on the resin structure are maintained. Therefore, the copolymer (A) of the present invention can be designed to have a regular structure and a high hydroxyl group (OH) content on the resin structure as compared with the conventional resin/linear organopolysiloxane condensation product. For example, in the case of a reaction product of a polysiloxane resin of the MQ type having a known hydroxyl group and a chain polysiloxane having a hydrolyzable terminal such as a hydroxyl group, the condensation reaction between the resins and the condensation reaction of the chain polysiloxane proceed competitively, the hydroxyl group is consumed in the reaction between the resins, and a random intermolecular bond tends to be formed, so that the affinity with other cosmetic raw materials and the film-forming ability may be lowered as compared with the copolymer (A) of the present invention.

More specifically, it is preferable that the copolymer (A) has $SiO_{4/2}$ units and 15 mol % or more of all $SiO_{4/2}$ units have hydroxyl groups on Si atoms. The $SiO_{4/2}$ unit (Q) is a siloxane unit mainly constituting a resin structure, and the high proportion of the Q unit having a hydroxyl group on the Si atom means that a large number of hydrophilic functional groups are included in the resin portion of the polymer (A), and the affinity with other cosmetic raw materials and the film-forming property are improved. In this respect, preferably 20 mol % or more, more preferably 25 mol % or more, and most preferably 27.5 to 40.0 mol % of all $SiO_{4/2}$ units of the copolymer (A) have hydroxyl groups on Si atoms. Even when a polysiloxane resin having a large number of hydroxyl groups is used as a raw material, the amount of hydroxyl groups decreases and the molecular structure of the copolymer randomizes when a large number of condensation reactions between resin raw materials proceed at the time of forming the copolymer (A), so that the copolymer (A) has the partial structure (T-Dn) described above, and it is particularly preferable that the copolymer (A) has a regular resin-linear structure.

[Weight-Average Molecular Weight of the Total Copolymer (A)]

The copolymer (A) is preferably composed of a resin structure (A1) block and a linear structure (A2) block bonded by the above-mentioned connecting structure, and the molecular weight distribution thereof can be controlled to some extent by the organopolysiloxane resin as a raw material, the chain diorganopolysiloxane, and the degree of condensation reaction, but from the viewpoint of the function as a film-forming agent used in cosmetics or external preparations and compatibility with other raw materials, it is preferable that the weight-average molecular weight specified from the molecular weight distribution using styrene polymer as a standard is in the range of 5,000 to 100,000, and particularly preferable is in the range of 10,000 to 50,000, and in the range of 12,000 to 40,000. The cosmetic composition or the preparation for external use of the present invention may be combined with two or more copolymers (A) having different structures or molecular weight distributions.

[Mass Ratio of Resin/Linear Structure Block of Copolymer (A)]

The copolymer (A) is composed of a resin structure (A1) block and a linear structure (A2) block bonded by the above-mentioned connecting structure, and the mass ratio of both blocks in the molecule can be controlled by the amount of the organopolysiloxane resin and the chain diorganopolysiloxane used as raw materials. Suitably, the organopolysiloxane resin constituting the resin structure (A1) block and the chain diorganopolysiloxane constituting the linear structure (A2) block can be reacted at a mass ratio of 10:90 to 95:5, and from the viewpoint of film-forming property of the obtained copolymer (A), an excess of the resin, that is, a mass ratio of 50:50 to 95:5 is preferable, and a mass ratio of 60:40 to 90:10 is particularly preferable. When the mass ratio of the resin structure (A1) block in the molecule is within the above-mentioned range as derived from the raw material, the film-forming property which is hard and excellent in feeling of use with little tackiness is realized, while maintaining followability and flexibility of the film derived from the linear structure (A2) block. Incidentally, in the case of a resin-linear organopolysiloxane block copolymer having no $R^1SiO_{3/2}$ units in the molecules thereof, even within the above-mentioned mass ratio, the film-forming property is insufficient, and the tackiness of the film, the lowering of the affinity with other cosmetic raw material components, and the like may occur.

[Compatibility of Copolymer (A)]

The present copolymer (A) is excellent in compatibility with other oleophilic cosmetic raw materials used in a cosmetic composition or a preparation for external use, and when used in combination with a solvent (B) described later, it has a feature that it has compatibility with various cosmetic raw materials of ½ or more of the mass of the copolymer (A) and the film-forming performance thereof does not deteriorate. For example, for a representative and general purpose oleophilic cosmetic raw material, cinnamic acid methyl ester, in particular, or octyl methoxycinnamate (p-methoxycinnamate ethylhexyl cinnamate), the copolymer (A) exhibits solubility in the presence of the solvent (B) described below, and for a 20 mass % solution of the solvent (B), uniformly dissolved with cinnamic acid methyl ester having the same mass as that of the present copolymer (A) in the solution, preferably 1.2 times, more preferably 1.5 times or more, it is preferable that separation and precipitation of cinnamic acid methyl ester do not occur over time. Having such properties, the copolymer (A) has the advantage of being usable in a wide range of dosage forms and formulations as a film-forming agent because of the high degree of freedom of formulation design as a cosmetic raw material and the excellent blending stability compared with the copolymer having a conventionally known resin-linear structure within the same molecule.

[Solvent (B)]

The cosmetic composition or the preparation for external use is characterized by containing the copolymer (A) described above, and since the copolymer (A) is in a solid to viscous semi-solid state at room temperature, it is preferable to blend the copolymer (A) in a form dissolved in the solvent (B) from the viewpoint of handling workability. Since the copolymer (A) is excellent in affinity with other cosmetic raw materials and has high solubility, the solvent (B) can utilize a physiologically acceptable oil agent without any particular limitation, and in particular, it is preferable that the solvent (B) is at least one kind in a liquid state at 5 to 100° C. selected from the group consisting of silicone oil, non-polar organic compound, and low polarity organic compound, and it may be a combination of two or more kinds. In addition, from the viewpoint of the feeling of use of the cosmetic composition or the preparation for external use of the present invention and the workability when the copolymer (A) is handled as a cosmetic raw material, the solvent (B) is preferably a volatile solvent (B1), and in particular, a solvent containing a volatile silicone oil is particularly preferable.

Silicone oils are hydrophobic, and their molecular structure may be cyclic, linear, or branched. The viscosities of silicone oils at 25° C. are usually in the range of 0.65 to 100,000 mm2/s, preferably in the range of 0.65 to 10,000 mm2/s.

Silicone oils include, for example, linear organopolysiloxanes, cyclic organopolysiloxanes, and branched organopolysiloxanes. Among these, volatile linear organopolysiloxanes, cyclic organopolysiloxanes, and branched organopolysiloxanes are preferable, and octamethylcyclotetrasiloxane (D4), decamethylcyclopentasiloxane (D5), or chain dimethylpolysiloxane having viscosities ranging from 0.65 to 10 mm2/s at 25° C. are particularly preferable as initial dispersing solvents of the present polymer (A).

More specifically, examples of linear organopolysiloxanes include dimethylpolysiloxane capped at both molecular chain ends with trimethylsiloxy groups (dimethylsilicone having low viscosity such as 2 mPas or 6 mPas to high viscosity of 1,000,000 mPa·s), organohydrogenpolysiloxane, methylphenylpolysiloxane capped at both molecular chain ends with trimethylsiloxy groups, dimethylsiloxane/methylphenylsiloxane copolymer capped at both molecular chain ends with trimethylsiloxy groups, diphenylpolysiloxane capped at both molecular chain ends with trimethylsiloxy groups, dimethylsiloxane/diphenylsiloxane copolymer capped at both molecular chain ends with trimethylsiloxy groups, trimethylpentaphenyl trisiloxane, phenyl (trimethylsiloxy) siloxane, methyl alkyl polysiloxane capped at both molecular chain ends with trimethylsiloxy groups, dimethylpolysiloxane/methylalkylsiloxane copolymer capped at both molecular chain ends with trimethylsiloxy groups, dimethylsiloxane/methyl (3,3,3-trifluoropropyl) siloxane capped at both molecular chain ends with trimethylsiloxy groups, α,ω-dihydroxypolydimethylsiloxane, α,ω-diethoxypolymethylsiloxane, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyltrisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, higher alkoxy modified silicones, higher fatty acid modified silicones, dimethiconol and the like.

Examples of cyclic organopolysiloxanes include hexamethylcyclotrisiloxane (D3), octamethylcyclotetrasiloxane (D4), decamethylcyclopentasiloxane (D5), dodecamethylcyclotetrasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl) trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, 1,3,5,7-tetra(N,N-bis(lauroyl)-3-aminopropyl) tetramethylcyclotetrasiloxane, and the like.

Examples of the branched organopolysiloxane include methyltristrimethylsiloxysilane, ethyltristrimethylsiloxysilane, propyltristrimethylsiloxysilane, tetrakistrimethylsiloxysilane, phenyltristrimethylsiloxysilane, and the like.

As the nonpolar organic compound and the low polarity organic compound, a hydrocarbon oil and a fatty acid ester oil are preferable. These are components which are widely used, in particular, as substrates for make-up cosmetics.

Examples of the hydrocarbon oil include liquid paraffin, light liquid isoparaffin, heavy liquid isoparaffin, petrolatum, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene polypropylene wax, scralan, squalene, pristane, polyisoprene, and the like.

Examples of fatty acid ester oils include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyl octanoate, cetyl lactate, myristyl lactate, diethyl phthalate, dibutyl phthalate, lanolin acetate, propylene glycol dioleate, glyceryl tri-2-ethylhexanoate, trimethylolpropane tri 2-ethylhexanoate, ditrimethylol propane triethylhexanoate, (isostearic acid/sebacic acid) ditrimethylolpropane, trimethylolpropane trioctanoate, trimethylolpropane triisostearate, diisopropyl adipate, diisobutyl adipate, 2-hexyldecyl adipate, di-2-heptylundecyl adipate, diisostearyl malate, monoisostearic acid hydrogenated castor oil, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearylate, dipentaerythrityl fatty acid ester, 2-hexyldecyl myristate, ethyl laurate, N-lauroyl-L-glutamic acid-2-octyldodecyl ester, N-lauroyl-L-glutamic acid di(cholesteryl/behenyl/octyldodecyl), N-lauroyl-L-glutamic acid di(cholesteryl/octyldodecyl), N-lauroyl-L-glutamic acid di(phytosteryl/behenyl/octyldodecyl), N-lauroyl-L-glutamic acid di(phytosteryl/octyldodecyl), N-lauroylsarcosine isopropyl, diisostearyl malate, neopentyl glycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, hydrogenated rosin pentaerythrityl, pentaerythrityl triethylhexanoate, dipentaerythrityl (hydroxystearic acid/stearic acid/rosin acid), polyglyceryl tetraisostearate, polyglyceryl nona-isostearate-10 triethylhexanoate, deca (erucic acid/isostearic acid/ricinoleic acid) polyglyceryl-8, (hexyldecanoic acid/sebacic acid) diglyceryl oligoester, glycol distearate (ethylene glycol distearate), diisopropyl dimer dilinoleate, diisostearyl dimer dilinoleate, (isostearyl/phytosteryl) dimer dilinoleate, (phytosteryl/behenyl) dimer dilinoleate, (phytosteryl/isostearyl/cetyl/behenyl) dimer dilinoleate, dimer dilinoleyl dimer dilinoleate, dimer dilinoleyl diisostearate, hydrogenated rosin condensation product of dimer dilinoleic acid hydrogenated castor oil, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, tri(caprylic acid/capric acid) glyceryl, tri(caprylic acid/capric acid/myristic acid/stearic acid) glyceryl, hydrogenated rosin triglyceride (hydrogenated ester gum), rosin triglyceride (ester gum), eicosan diacid behenate, glyceryl di-2-heptylundecanoate, diglyceryl myristate isostearate, cholesteryl acetate, cholesteryl nonanoate, cholesteryl stearate, cholesteryl isostearate, cholesteryl oleate, diglyceryl myristate, cholesteryl acetate, cholesteryl 12-hydroxystearate, cholesteryl macadamiate, phytosteryl macadamiate, phytosteryl isostearate, soft lanolin fatty acid cholesteryl, hard lanolin fatty acid cholesteryl, long chain branched fatty acid cholesteryl, long chain α-hydroxy fatty acid cholesteryl, octyl dodecyl ricinoleate, octyl dodecyl lanolin fatty acid, octyldodecyl erucate, isostearic acid hydrogenated castor oil, avocado oil fatty acid ethyl, lanolin fatty acid isopropyl, and the like.

For example, higher alcohols having 10 to 30 carbon atoms can be used as the low polarity organic compound. When a higher alcohol is used as the emulsion stabilizing component, the amount of hydrophilic surfactant can be reduced, and the water resistance can be further improved. The higher alcohol is a saturated or unsaturated monohydric aliphatic alcohol, and the hydrocarbon group portion may be either linear or branched, but is more preferably linear. Examples of higher alcohols having 10 to 30 carbon atoms include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, lanolin alcohol, hydrogenated lanolin alcohol, and the like. In the present invention, it is preferable to use a higher alcohol having a melting point of 40 to 80° C. alone, or to combine a plurality of higher alcohols so that the melting point is 40 to 70° C.

The solvent (B) may be added to the cosmetic composition or the preparation for external use of the present invention as the initial dispersion solvent of the copolymer (A), may be added to other components or as independent components, and the type/combination thereof is not particularly limited. In the cosmetic composition or the preparation for external use of the present invention, it is preferable to include a volatile solvent (B1) as an initial dispersion solvent of the copolymer (A), but a non-volatile solvent (B) may be added as another oil agent. The blending amount is not particularly limited, but is preferably from 3 to 60 mass %, more preferably from 4 to 50 mass %, and still more preferably from 5 to 40 mass %, based on the total mass of the cosmetic composition or the preparation for external use.

In addition to the above, oils and fats, higher alcohols, higher fatty acids, fluorine-based oils, and the like may be used as solvents depending on the type and dosage form of the cosmetic composition or the preparation for external use, or two or more of these may be used in combination. These solvents can be used without limitation, for example, those exemplified in paragraphs 0066 to 0069 of JP 2014-040512 A and the like.

[Oleophilic Cosmetic Raw Material (C)]

(C) An oleophilic cosmetic raw material is not particularly limited as long as it is an oleophilic raw material used in a cosmetic material/external preparation and is other than the above-mentioned solvent (B), but one or more selected from the group consisting of (C1) an ultraviolet protection component, (C2) a thickening/gelling agent, (C3) a silicone exhibiting a gummy state at room temperature (silicone gum), (C4) a silicone resin, (C5) a crosslinkable organopolysiloxane, (C6) an organo-modified silicone, (C7) an organo-modified clay mineral, (C8) a physiologically active component, and (C9) a perfume and a dye are exemplified. In particular, the copolymer (A) according to the present invention disclosure is excellent in compatibility with these oleophilic cosmetic raw materials, in particular, organic ultraviolet protection components, and can uniformly dissolve even a small amount of most organic ultraviolet protection components such as salicylic acid-based, PABA-based, benzophenone-based, cinnamic acid-based, and benzoylmethane-based and the like. In particular, since the ultraviolet protection component corresponding to UV-B such as octyl methoxycinnamic acid and the ultraviolet protection component corresponding to UV-A such as diethylaminohydroxybenzoyl benzoic acid are highly compatible with each other, even when a plurality of ultraviolet protection components are combined and blended, the blending stability is not lowered.

<(C1) Ultraviolet Protection Component>

The ultraviolet protection component includes an inorganic ultraviolet protection component and an organic ultraviolet protection component. When the cosmetic composition or the preparation for external use of the present invention is a sunscreen cosmetic, it is preferable to contain at least one inorganic or organic, in particular, an organic ultraviolet protection component. The copolymer (A) of the present invention is not only excellent in compatibility with the above-mentioned cinnamic acid methyl ester, in particular, octyl methoxycinnamate, but is also excellent in compatibility with generally poorly soluble organic ultraviolet protective components such as hexyl diethylaminohydroxybenzoyl benzoate known as "Uvinul A", bis-ethylhexyloxyphenol methoxyphenyl triazine known as "Tinosorb S", 2-cyano-3,3-diphenylpropa-2-enoic acid 2-ethylhexyl ester known as "Octocrylene", and other ultraviolet absorbing agents, and can improve freedom of formulation design and blending stability.

Examples of the inorganic ultraviolet protection component include metal oxides such as titanium oxide, zinc oxide, cerium oxide, low-order titanium oxide, and iron-doped titanium oxide; metal hydroxides such as iron hydroxide; metal flakes such as plate iron oxide and aluminum flakes; and ceramics such as silicon carbide. Of these, at least one selected from particulate, plate-like, needle-like or fiber-like fine particulate metal oxides and fine particulate metal hydroxides having an average particle diameter in the range of 1 to 100 nm is particularly preferable. It is preferable that these powders are conventionally subjected to known surface treatments, for example, fluorine compound treatment (preferably perfluoroalkyl phosphate treatment, perfluoroalkyl silane treatment, perfluoropolyether treatment, fluorosilicone treatment, fluorinated silicone resin treatment), silicone treatment (preferably methyl hydrogen polysiloxane treatment, dimethyl polysiloxane treatment, gas phase tetramethyl tetrahydrogen cyclotetrasiloxane treatment), silicone resin treatment (preferably trimethyl siloxysilicate treatment), pendant treatment (adding an alkyl chain or the like after vapor phase process silicone treatment), silane coupling agent treatment, titanium coupling agent treatment, silane treatment (preferably alkylsilane or alkylsilazane treatment), oil agent treatment, N-acylated lysine treatment, polyacrylic acid treatment, metal soap treatment (preferably stearic acid or myristic acid salt), acrylic resin treatment, metal oxide treatment and the like, and it is preferable that treatment with a plurality of these treatments is performed. For example, the surface of the fine particulate titanium oxide may be coated with a metal oxide such as silicon oxide or alumina, followed by surface treatment with alkylsilane, or the like. The surface treatment amount is preferably in the range of 0.1 to 50 mass % in total with respect to the powder.

The organic ultraviolet protection component is an oleophilic ultraviolet protection component, for example, benzoic acid-based ultraviolet absorbers such as para-aminobenzoic acid (hereinafter abbreviated as PABA), PABA monoglycerine ester, N,N-dipropoxy PABA ethyl ester, N, N-diethoxy PABA ethyl ester, N,N-dimethyl PABA ethyl ester, N,N-dimethyl PABA butyl ester, hexyl diethylaminohydroxybenzoyl benzoate; anthranilic acid-based ultraviolet absorbers such as homomenthyl-N-acetylanthranilate; salicylic acid-based ultraviolet absorbers such as amyl salicylate, menthyl salicylate, homomenthyl salicylate, octyl salicylate, phenyl salicylate, benzyl salicylate, p-isopropanol phenyl salicylate; cinnamic acid-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethylhexanoyl-dipalmethoxy cinnamate, 3,4,5-trimethoxycinnamic acid 3-methyl-4-[methylbis (trimethylsiloxy) silyl] butyl; benzophenone-based ultraviolet absorbers such as 2,4'-dihydroxybenzophenone, 2,2'-dihydroxy-4-methoxybenzophenone, 2,2'-dihydroxy-4,4'-dimethoxybenzophenone, 2,2', 4,4'-tetrahydroxybenzophenone, 2-hydroxy-4-methoxybenzophenone, 2-hydroxy-4-methoxy-4'-methylbenzophenone, 2-hydroxy-4 methoxybenzophenone-5-sulfonate, 4-phenylbenzophenone, 2-ethylhexyl-4'-phenyl-benzophenone-2-carboxylate, hydroxy-4-n-octoxybenzophenone, 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenylbenzotriazole, 2-(2'-hydroxy-5'-tert-octylphenyl) benzotriazole, 2-(2'-hydroxy-5'-methylphenylbenzotriazole, dibenzalazine, dianisoylmethane, 4-methoxy-4'-tert-butyldibenzoylmethane, 5-(3,3-dimethyl-2-norbornylidene)-3-pentan-2-one and the like are exemplified.

It is also possible to use a polymer powder containing the organic ultraviolet protection component in a hydrophobic polymer powder. The polymer powder may or may not be hollow, the average primary particle size thereof may be in the range of 0.1 to 50 μm, and the particle size distribution may be broad or sharp. Examples of the polymer include acrylic resin, methacrylic resin, styrene resin, polyurethane resin, polyethylene, polypropylene, polyethylene terephthalate, silicone resin, nylon, acrylamide resin, and silylated polypeptide resin. The polymer powder containing organic ultraviolet protection components ranging from 0.1 to 30 mass % is preferred, particularly preferred is the polymer powder containing 4-tert-butyl-4'-methoxydibenzoylmethane, which is a UV-A absorber.

In the cosmetic composition of the present invention, the ultraviolet protection component which can be suitably used is at least one selected from the group consisting of fine particulate titanium oxide, fine particulate zinc oxide, paramethoxycinnamic acid 2-ethylhexyl, 4-tert-butyl-4'-methoxydibenzoylmethane, hexyl diethylamino hydroxybenzoylbenzoate, bis-ethylhexyloxyphenol methoxyphenyl triazine, 2-cyano-3,3-diphenylpropa-2-enoic acid 2-ethylhexyl ester, and other benzophenone-based ultraviolet absorbers. These ultraviolet protection components are generally used, are easily available, and have a high ultraviolet protection effect, so that they can be suitably used. In particular, it is preferable to use a combination of an inorganic-based and an organic-based ultraviolet protection component, and it is more preferable to use a combination of an ultraviolet protection component corresponding to UV-A and an ultraviolet protection component corresponding to UV-B.

<(C2) Thickening/Gelling Agent>

The thickening/gelling agent is a component for thickening or gelling the oil agent which is above-mentioned solvent (B) and other oleophilic cosmetic raw materials, and includes metal soaps such as aluminum stearate, magnesium stearate, zinc myristate, amino acid derivatives such as N-lauroyl-L-glutamic acid, α, γ-di-n-butylamine, dextrin fatty acid ester such as dextrin palmitate ester, dextrin stearate ester, dextrin 2-ethylhexanoic acid palmitate ester, sucrose fatty acid ester such as sucrose palmitate ester and sucrose stearic acid ester, benzylidene derivatives of sorbitol such as monobenzylidene sorbitol and dibenzylidene sorbitol, and the like. One or two or more of these can be used as necessary.

<(C3) Silicone Gum>

Silicone gum is a linear diorganopolysiloxane with an ultrahigh degree of polymerization, and is also referred to as a silicone raw rubber or an organopolysiloxane gum. Silicone raw rubbers are distinguished from the oily silicones described above in that they have a measurable degree of plasticity due to their high degree of polymerization. Examples of such raw silicone rubbers include substituted or unsubstituted organopolysiloxanes having dialkylsiloxy units (D unit) such as dimethylpolysiloxane, methylphenylpolysiloxane, aminopolysiloxane, methylfluoroalkylpolysiloxane, and those having microcrosslinking structures thereof, and a representative example thereof is represented by the general formula: $R^{10}$ $(CH_3)_2SiO)_s\{(CH_3)_2SiO)_s\{(CH_3)R^{11}SiO\}_t Si(CH_3)_2R^{10}$ (wherein $R^{11}$ represents a vinyl group, a phenyl group, an alkyl having 6 to 20 carbon atoms, an aminoalkyl group having 3 to 15 carbon atoms, a perfluoroalkyl group having 3 to 15 carbon atoms, a quaternary ammonium salt group-containing alkyl group having 3 to 15 carbon atoms, and the end group $R^{10}$ is a group selected from an alkyl group having 1 to 8 carbon atoms, a phenyl group, a vinyl group, an aminoalkyl group having 3 to 15 carbon atoms, a hydroxyl group and an alkoxy group having 1 to 8 carbon atoms, and s=2,000 to 6,000, t=0 to 1,000, s+t=2,000 to 6,000). Among them, dimethylpolysiloxane raw rubbers having a degree of polymerization of 3000 to 20000 are preferable.

<(C4) Silicone Resin>

The silicone resin is an organopolysiloxane having a highly branched structure, a net-like structure, or a cage-like structure, and is in a liquid state or a solid state at room temperature, and may be any silicone resin commonly used in cosmetics or external preparations, as long as it is not inconsistent with the object of the present invention. Examples of solid silicone resin include MQ resin, MDQ resin, MTQ resin, MDTQ resin, TD resin, TQ resin, and TDQ resin consisting of triorganosiloxy units (M unit) (organo groups are methyl groups only, methyl groups and vinyl groups or phenyl groups), diorganosiloxy units (D unit) (organo groups are methyl groups only, methyl groups and vinyl groups or phenyl groups), monoorganosiloxy units (T unit) (organo groups are methyl groups, vinyl groups, or phenyl groups), and siloxy units (Q unit). Further, trimethylsiloxysilicate, polyalkylsiloxysilicate, trimethyl siloxysilicate containing dimethylsiloxy units, and alkyl (perfluoroalkyl) siloxysilicate are exemplified. It is particularly preferable that these silicone resins are oil-soluble and can be dissolved in D4 and D5.

<(C5) Crosslinkable Organopolysiloxane>

As the crosslinkable organopolysiloxane, a non-emulsifying organopolysiloxane having a structure in which an organopolysiloxane chain is three-dimensionally cross-linked by reaction with a crosslinkable component or the like and does not have a hydrophilic part such as a polyoxyalkylene unit is preferable. Such crosslinkable organopolysiloxanes can be used without limitation irrespective of physical forms such as dilutions and properties and methods of preparation, and α,ω-diene cross-linked silicone elastomers described in U.S. Pat. No. 5,654,362 (commercially available products are DC 9040 Silicone Elastomer Blend, DC 9041 Silicone Elastomer Blend, DC 9045 Silicone Elastomer Blend, DC 9046 Silicone Elastomer Blend manufactured by Dow Corning Corporation, USA) are particularly preferred.

<(C6) Organo-Modified Silicone>

The organo-modified silicone is an oleophilic organo-modified silicone and functions as an oil agent or additive. Specific examples include amino modified silicones, amino polyether modified silicones, epoxy modified silicones, carboxyl modified silicones, amino acid modified silicones, carbinol modified silicones, acrylic modified silicones, phenol modified silicones, amidoalkyl modified silicones, amino glycol modified silicones, and alkoxy modified silicones. The organo-modified silicones may have an alkylene chain, an aminoalkylene chain or a polyether chain to such an extent that the compound does not have hydrophilicity, in addition to the polysiloxane bond as the main chain, and the organo-modified group may have one or both of the side chain and the end of the polysiloxane chain. When the cosmetic composition of the present invention is used as a hair cosmetics, amino modified silicones, carbinol modified silicones, aminopolyether modified silicones or aminoglycol modified silicones can be suitably used, and amino modified silicones having a 3-aminopropyl group, an N-(2-aminoethyl)3-aminopropyl group or the like can be exemplified as general examples.

<(C7) Organo-Modified Clay Mineral>

Examples of the organo-modified clay mineral include dimethylbenzyldodecylammonium montmorillonite clay, dimethyldioctadecylammonium montmorinite clay, dimethylalkylammonium hectorite, benzyldimethyl stearylammonium hectorite, distearyldimethylammonium aluminum magnesium chloride-treated magnesium aluminum silicate, and the like. These commercially available products include Benton 27 (hectorite treated with benzyl dimethyl stearyl ammonium chloride, manufactured by National red Co.) and Benton 38 (hectorite treated with distearyl dimethyl ammonium chloride, manufactured by National red Co.).

<(C8) Bioactive Component>

Examples include bioactive components that impart some bioactivity to the skin when applied to the skin and are lipophilic. Example thereof include an anti-inflammatory agent, an antiaging agent, a tightening agent, a hair growth agent, a hair tonic, a humectant, a circulation promoter, a desiccant, a cooling agent, a warm sensation agent, vitamins, amino acids, a wound healing-promotion agent, irritation mitigation agent, an analgesic, a cell activating agent, an enzyme component, and the like, which are lipophilic. Among them, a natural plant extraction component, a seaweed extraction component, and a crude drug component which are oleophilic are particularly preferable.

<(C9) Perfume and Dye>

The perfume is not particularly limited as long as it is an oleophilic perfume, and examples thereof include a perfume extracted from flowers, seeds, leaves, roots and the like of various plants, a perfume extracted from seaweeds, a perfume extracted from each site or secretion of an animal (e.g., gypsum, macco), and an artificially synthesized perfume (e.g., menthol, musk, acetate ester, vanilla). The perfume is blended into the cosmetic composition or the preparation for external use of the present invention to impart fragrance, flavor, or to mask offensive odors. The dyes include oil-soluble dyes, constitutive pigments, inorganic pigments, organic pigments, oleophilic fluorescent brighteners, and the like. These oleophilic dye components can be stably dispersed in the cosmetic composition or the preparation for external use of the present invention to achieve uniform and beautiful color development and coloration.

[Surfactant (D)]

The cosmetic composition or the preparation for external use of the present invention preferably contains at least one surfactant. Surfactants can be one or two or more combined surfactants selected from the group consisting of anionic surfactants, cationic surfactants, nonionic surfactants (including silicone-based surfactants), amphoteric surfactants, and semipolar surfactants. These surfactants may be used as a detergent component, a disinfecting component of a cosmetic or external preparation, or may be used as a dispersant or an emulsifier of various cosmetic raw material components.

More particularly, examples of anionic surfactants include saturated or unsaturated fatty acid salts (such as sodium laurate, sodium stearate, sodium stearate, sodium oleate, sodium linoleate), alkyl sulfate, alkylbenzenesulfonic acid (such as hexylbenzenesulfonic acid, toccylbenzenesulfonic acid, dodecylbenzenesulfonic acid) and salts thereof, polyoxyalkylene alkyl ether sulfate, polyoxyalkylene alkenyl ether sulfate, polyoxyethylene alkyl sulfuric ester salt, sulfosuccinic acid alkyl ester salt, polyoxyalkylene sulfosuccinic acid alkyl ester salt, polyoxyalkylene alkyl phenyl ether sulfate, alkanesulfonate, octyltrimethylammonium hydroxide, dodecyltrimethylammonium hydroxide, alkylsulfonate, polyoxyethylene alkylphenyl ether sulfate, polyoxyalkylene alkyl ether acetate, alkyl phosphate, polyoxyalkylene alkyl ether phosphate, acyl glutamate, α-acyl sulfonate, alkylsulfonate, alkylarylsulfonate, α-olefinsulfonate, alkylnaphthalenesulfonate, alkanesulfonate, alkyl or alkenyl sulfonate, alkyl or alkenyl sulfate, alkylamidosulfate, alkyl or alkenyl phosphate, alkyloyl alkyl taurine salt, N-acyl amino acid salt, sulfosuccinate, alkyl ether carboxylate, amide ether carboxylate, α-sulfo fatty acid ester salt, alanine derivative, glycine derivative, and arginine derivative.

Examples of the salts include an alkali metal salt such as a sodium salt, an alkaline earth metal salt such as a magnesium salt, an alkanolamine salt such as a triethanolamine salt, and an ammonium salt.

Examples of cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dichocoyl dimethylammonium chloride, dioctyldimethylammonium chloride, di (POE) oleylmethylammonium chloride (2EO), benzalkonium chloride, alkyl benzalkonium chloride, alkyl dimethyl benzalkonium chloride, benzalkonium alkylammonium chloride, benzethonium chloride, stearyl dimethyl benzyl ammonium chloride, lanolin-derived quaternary ammonium salt, diethylaminoethyl stearamide, diethylaminoethylamide stearate, dimethylaminopropylamide stearate, behenic acid amidopropyldimethylhydroxypropylammonium chloride, stearoylcollaminoformylmethylpyridinium chloride, cetylpyridinium chloride, tall oil alkylbenzylhydroxyethyl imidazolinium chloride, and benzylammonium salts.

Examples of nonionic surfactants include polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkyl phenols, polyoxyalkylene alkyl phenyl ethers, polyoxyalkylene phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerin fatty acid esters, polyglycerin alkyl ethers, polyglycerin fatty acid esters, sucrose fatty acid esters, fatty acid alkanolamides, alkyl glucosides, polyoxyalkylene fatty acid bisphenyl ethers, polypropylene glycols, diethylene glycols, fluorinated surfactants, polyoxyethylene/polyoxypropylene block polymers, and alkyl polyoxyethylene/polyoxypropylene block polymer ethers.

Typical examples of the silicone-based surfactants include polyoxyalkylene modified silicone, polyglyceryl modified silicone, glyceryl modified silicone, sugar modified silicone, polyoxyethylene/polyoxypropylene block polymer, and alkylpolyoxyethylene/polyoxypropylene block polymer ether. Examples of preferable silicone-based surfactants include linear polyoxyalkylene-modified organopolysiloxane (polyether-modified silicone bonded to polyoxyalkylene group at the side chain and/or end), block copolymer-type polyoxyalkylene-dimethylpolysiloxane copolymer, and linear polyoxyalkylene-alkyl comodified organopolysiloxane (alkyl/polyether-modified silicone bonded to polyoxyalkylene groups and alkyl groups at the side chain and/or end). In addition, certain elastomeric silicone polyethers described in Japanese Patent No. 4080597 (JP 11-49957 A), JP 2001-011281 A, and the like (commercially available products are DC 9011 Silicone Elastomer Blend, manufactured by Dow Corning Corporation, U.S.A.) are also preferably exemplified.

Examples of amphoteric surfactants include imidazoline type, amidobetaine type, alkylbetaine type, alkylamidobetaine type, alkylsulfobetaine type, amidosulfobetaine type, hydroxysulfobetaine type, carbobetaine type, phosphobetaine type, aminocarboxylic acid type, and amido amino acid type amphoteric surfactants. Specifically, imidazoline-type amphoteric surfactants such as 2-undecyl-N,N—N—(hydroxyethyl carboxymethyl)-2-imidazoline sodium, 2-cocoil-2-imitazolinium hydroxide-1-carboxyethyloxy disodium salt; alkyl betaine-type amphoteric surfactants such as lauryl dimethylaminoacetate betaine and myristyl betaine; amidobetaine amphoteric surfactant such as coconut oil fatty acid amide propyldimethylaminoacetic acid betaine, palm kernel oil fatty acid amido propyldimethylaminoacetic acid betaine, beef tallow fatty acid amido propyldimethylaminoacetic acid betaine, hydrogenated beef tallow fatty acid amido propyldimethylaminoacetic acid betaine, lauric acid amido propyldimethylaminoacetic acid betaine, myristic acid amido propyldimethylaminoacetic acid betaine, palmitic acid amido propyldimethylaminoacetic acid betaine, stearic acid amido propyldimethylaminoacetic acid betaine, oleic acid amido propyldimethylaminoacetic acid betaine; phosphobetaine-type amphoteric surfactants such as lauryl hydroxyphosphobetaine; amido amino acid-type amphoteric surfactants such as N-lauroyl-N'-hydroxyethyl-N'-carboxymethylethylenediamine sodium, N-oleoyl-N'-hydroxyethyl-N'-carboxymethylethylenediamine sodium, N-cocoyl-N'-hydroxyethyl-N'-carboxymethylethylenediamine sodium, N-lauroyl-N'-hydroxyethyl-N'-carboxymethylethylenediamine potassium, N-oleoyl-N'-hydroxyethyl-N'-carboxymethylethylenediamine potassium, N-lauroyl-N-hydroxyethyl-N'-carboxymethylethylenediamine sodium, N-oleoyl-N-hydroxyethyl-N'-carboxymethylethylenediamine sodium, N-cocoyl-N-hydroxyethyl-N'-carboxymethylethylenediamine sodium, N-lauroyl-N-hydroxyethyl-N',N'-dicarboxymethylethylenediamine monosodium, N-oleoyl-N-hydroxyethyl-N',N'-dicarboxymethylethylenediamine monosodium, N-cocoyl-N-hydroxyethyl-N',N'-dicarboxymethylethylenediamine monosodium, N-lauroyl-N-hydroxyethyl-N',N'-dicarboxymethylethylenediamine disodium, N-oleoyl-N-hydroxyethyl-N',N'-dicarboxymethylethylenediamine disodium, and N-cocoyl-N-hydroxyethyl-N',N'-dicarboxymethylethylenediamine disodium are exemplified.

Examples of the semipolar surfactants include alkylamine oxide type surfactants, alkylamine oxide, alkylamidoamine oxide, alkylhydroxyamine oxide, and the like, and alkyldimethylamine oxide having 10 to 18 carbon atoms, alkoxyethyldihydroxyethylamine oxide having 8 to 18 carbon atoms, and the like are preferably used. Specifically, dodecyl dimethylamine oxide, dimethyl octylamine oxide, diethyl decylamine oxide, bis-(2-hydroxyethyl) dodecylamine oxide, dipropyl tetradecylamine oxide, methyl ethyl hexadecylamine oxide, dodecyl amidopropyl dimethylamine oxide, cetyl dimethylamine oxide, stearyl dimethylamine oxide, tallow dimethylamine oxide, dimethyl-2-hydroxyoctadecylamine oxide, lauryl dimethylamine oxide, myristyl dimethylamine oxide, isostearyl dimethylamine oxide, coconut fatty acid alkyldimethylamine oxide, caprylic acid amidopropyldimethylamine oxide, capric acid amidopropyldimethylamine oxide, lauric acid amidopropyldimethylamine oxide, myristic acid amidopropyldimethylamine oxide, palmitic acid amidopropyldimethylamine oxide, stearic acid amidopropyldimethylamine oxide, isostearic acid amidopropyldimethylamine oxide, oleic acid amidopropyldimethylamine oxide, ricinoleic acid amidopropyldimethylamine oxide, 12-hydroxystearic acid amidopropyldimethylamine oxide, coconut fatty acid amidopropyldimethylamine oxide, palm kernel oil fatty acid amidopropyldimethylamine oxide, castor oil fatty acid amidopropyldimethylamine oxide, lauric acid amidoethyldimethylamine oxide, myristic acid amidoethyldimethylamine oxide, coconut fatty acid amidoethyldimethylamine oxide, lauric acid amidoethyldiethylamine oxide, myristic acid amidoethyldiethylamine oxide, coconut fatty acid amidoethyldiethylamine oxide, lauric acid amidoethyldihydroxyethylamine oxide, myristic acid amidoethyl dihydroxyethylamine oxide, and coconut fatty acid amide ethyl dihydroxyethylamine oxide are exemplified.

[Powder or Colorant (E)]

The cosmetic composition or the preparation for external use of the present invention can further blend powder or colorant, particularly any powder used in cosmetic materials (including powder and pigment used as colorant).

Any powder or colorant can be used as long as it is used in a usual cosmetics, regardless of the shape thereof (such as spherical, rod-like, needle-like, plate-like, indefinite shape, and spindle-like), particle diameter (such as fume-like, fine particle, and pigment class), particle structure (such as porous and non-porous), and when these powder and/or colorant are blended as a pigment, it is preferable to blend one or more kinds selected from inorganic pigment powder, organic pigment powder, and resin powder having an average particle diameter in the range of 1 nm to 20 μm.

Specific examples of the powder or colorant include inorganic powder, organic powder, surfactant metal salt powder (metal soap), colored pigment, pearl pigment, metal powder pigment, silicone elastomer powder, and the like, and further composites of these can be used. These powder or colorant include those which function as ultraviolet protection components.

Specifically, inorganic powders include titanium oxide, zirconium oxide, zinc oxide, cerium oxide, magnesium oxide, barium sulfate, calcium sulfate, magnesium sulfate, calcium sulfate, magnesium carbonate, talc, mica, kaolin, sericite, muscovite, synthetic mica, phlogopite, lepidolite, biotite, lithia mica, silicic acid, silicic anhydride, aluminum silicate, sodium silicate, sodium magnesium silicate, magnesium silicate, magnesium aluminum silicate, calcium silicate, barium silicate, strontium silicate, metal tungstate, hydroxyapatite, vermiculite, hydrargilite, bentonite, montmorillonite, hectorite, zeolite, ceramic powder, dicalcium phosphate, alumina, aluminum hydroxide, boron nitride, boron nitride, and the like; organic powders include polyamide powder, polyester powder, polyethylene powder, and polypropylene powder, polystyrene powder, polyurethane powder, polystyrene powder, benzoganamine powder, polymethylbenzoganamine powder, polytetrafluoroethylene powder, polymethyl methacrylate powder, cellulose, silk powder, nylon powder, 12-nylon, 6-nylon, silicone powder, silicone rubber powder, silicone elastomer spherical powder coated with polymethyl silsesquioxane thereon, polymethylsilsesquioxane spherical powder, styrene/acrylic acid copolymer, divinylbenzene/styrene copolymer, vinyl resin, urea resins, phenol resin, fluororesin, silicon resin, acrylic resin, melamine resin, epoxy resin, polycarbonate resin, microcrystalline fiber powder, starch powder, lauroyl lysine and the like; surfactant metal salt powders include zinc stearate, aluminum stearate, calcium stearate, magnesium stearate, zinc myristate, magnesium myristate, zinc palmitate, zinc laurate, zinc cetyl phosphate, calcium cetyl phosphate, sodium zinc cetyl phosphate, and the like; colored pigments include inorganic red pigments such as red oxide, iron oxide, iron hydroxide, iron titanate, inorganic brown pigments such as γ-iron oxide, inorganic yellow pigments such as yellow iron oxide, black iron oxide, inorganic black pigments such as carbon black, inorganic purple pigments such as manganese violet, cobalt violet and the like, inorganic green pigments such as chromium hydroxide, chromium oxide, cobalt oxide, cobalt titanate and the like, inorganic blue pigments such as prussian blue, ultramarine blue and the like; those obtained by laking tar dyes such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207 and the like, or those obtained by laking natural dyes such as carmine acid, lacquemic acid, carthamine, braziline, chrosine and the like; pearl pigments such as titanium oxide-coated mica, titanated mica, iron oxide-treated titanated mica, titanium oxide-coated mica, bismuth oxychloride, titanium oxide-coated bismuth oxychloride, titanium oxide-coated talc, fish scale foil, titanium oxide-coated colored mica and the like; oxidized titanium oxide coated mica, oxychlorinated bismuth, titanium oxide coated bismuth oxychloride, titanium oxide coated tantalum foil, fish scaly foil, titanium oxide coated colored mica, and the like; metal powder pigments such as aluminum, gold, silver, copper, platinum, stainless steel, and the like.

The silicone elastomer powder is a crosslinked product of a liner diorganopolysiloxane mainly composed of a diorganosiloxy unit (D unit), and can be suitably obtained by crosslinking an organohydrogenpolysiloxane having a silicon-bonded hydrogen atom at the side chain or end and a diorganopolysiloxane having an unsaturated hydrocarbon group such as an alkenyl group at the side chain or end under a hydrosilylation reaction catalyst. Since the silicone elastomer powder is soft, elastic, and excellent in oil absorption compared to the silicone resin powder composed of T unit and Q unit, it can absorb oil and fat on the skin and prevent cosmetic collapse.

The silicone elastomer powder may have various shapes, such as spherical, flat, or indefinite. The silicone elastomer powder may be in the form of an oil dispersion. The cosmetic composition of the present invention is a silicone elastomer powder having a particle shape, a primary particle diameter thereof determined by observation using an electron microscope and/or an average primary particle diameter measured by laser diffraction/scattering method falls within a range of 0.1 to 50 μm and a silicone elastomer powder having a primary particle shape of spherical shape can be suitably blended. The silicone elastomer constituting the silicone elastomer powder is preferably a silicone elastomer having a hardness of 80 or less, more preferably 65 or less according to JIS K 6253 "Hardness testing method for rubber, vulcanized or thermoplastic" as measured by type-A durometer.

The silicone elastomer powder may optionally be subjected to a surface treatment with a silicone resin, silica, or the like. Examples of the surface treatment include those described in JP 2-243612 A, JP 8-12545 A, JP 8-12546 A, JP 8-12524 A, JP 9-241511 A, JP 10-36219 A, JP 11-193331 A, and JP 2000-281523 A. The silicone elastomer powder corresponds to the crosslinked silicone powder listed in the "Japanese Cosmetic Ingredients Codex". Commercial products of silicone elastomeric powders include, for example, Dow Corning Toray's Trefill E-506S, Trefill E-508, 9701 Cosmetic Powder, 9702 Powder, and the like.

Further, it is particularly preferable that a part or all of these powders or colorants are subjected to a water-repellent treatment. Further, these powders or colorants may be composited with each other, and silicone compounds other than the general oil agent, the organopolysiloxane copolymer according to the present invention, fluorine compounds, surfactants, or the like subjected to surface treatment may also be used, and one type or two or more types may be used as necessary. The blending amount of these powders or colorants is preferably in the range of 0.1 to 99 mass % of the total cosmetic agent. In particular, in the case of a powdery solid cosmetic, the blending amount is preferably in the range of 80 to 99 mass % of the whole cosmetic.

Examples of other water-repellent treatments include those in which the powder or colorant is treated with various water-repellent surface treatments, such as methyl hydrogen polysiloxane treatment, silicone resin treatment, silicone gum treatment, acrylic silicone treatment, organosiloxane treatment such as fluorinated silicone treatment, metal soap treatment such as zinc stearate treatment, silane coupling agent treatment, silane treatment such as alkylsilane treatment, fluorine compound treatment such as perfluoroalkyl phosphate ester salt, perfluoro-ether treatment, amino acid treatment such as N-lauroyl-L-lysine treatment, and acrylic acid treatment such as squalane treatment, and the like, and one or more of these can be used in combination.

It is preferable that the above-mentioned powder or colorant is treated using another powder dispersant or surface treatment agent, in particular, the powder or colorant may be dispersed or surface treated by the novel powder treating agent and treatment method proposed by the present inventors in WO 2009/022621, JP 2011-148784 A, JP 2011-149017 A, JP 2011-246704 A, JP 2011-246705 A, JP 2011-246706 A, WO 2009/022621, WO 2011/049246, WO 2011/049248, JP 2011-286973, and the like, or the powder or colorant may be treated with the new powder treatment agent and the oiling agent to form a slurry.

[Alcohols (F)]

The cosmetic composition or the preparation for external use of the present invention may further contain alcohols. The alcohols may be lower alcohols, polyhydric alcohols, or combinations thereof.

Lower alcohols are used as solvents, solubilizers or dispersing media for components of various cosmetics and external preparations. Such may also be blended for the purpose of cleaning, sterilization, convergence, promotion of drying and the like, and it is particularly preferable to blend such in a cosmetic which emphasizes a refreshed feel. Examples of the lower alcohols include ethanol, isopropanol, n-propanol, tert-butanol, sec-butanol, and the like, and in particular, ethanol is preferably used.

Polyhydric alcohols can be used as solvents for various components as well as lower alcohols, and are blended for the purpose of improving the moisturizing effect and the feeling of consistency. More specifically, the polyhydric alcohols include dihydric alcohols such as 1,3-butylene glycol, 1,2-butylene glycol, propylene glycol, trimethylene glycol, tetramethylene glycol, 2,3-butylene glycol, pentamethylene glycol, 2-butene-1,4-diol, dibutylene glycol, pentyl glycol, hexylene glycol, and octylene glycol; trihydric alcohols such as glycerin, trimethylolpropane, 1,2,6-hexanetriol; tetravalent or higher polyhydric alcohols such as pentaerythritol and xylitol; and sugar alcohols such as sorbitol, mannitol, maltitol, maltotriose, sucrose, erythritol, glucose, fructose, starch degradation products, maltose, xylitose, starch degradation sugar reduction alcohol, and the like. In addition to these low molecular weight polyhydric alcohols, polyhydric alcohol polymers such as diethylene glycol, dipropylene glycol, triethylene glycol, polypropylene glycol, tetraethylene glycol, diglycerin, polyethylene glycol, triglycerin, tetraglycerin, and polyglycerin, and the like are exemplified.

Preferable polyhydric alcohols are 1,3-butylene glycol, sorbitol, dipropylene glycol, glycerin, and polyethylene glycol, especially polyhydric alcohols selected from 1,3-butylene glycol, sorbitol, dipropylene glycol, glycerin, and polyethylene glycol are particularly preferably blended for the purpose of improving the moisturizing effect of cosmetics.

[Water]

The cosmetic composition or the preparation for external use of the present invention may be in the form of an emulsion or water-containing composition and may contain water. The water does not contain components harmful to the human body and may be clean, and examples thereof include tap water, purified water, ion-exchanged water, and mineral water. In addition, compositions containing alcohol at a high concentration have high flammability, but the inclusion of water lowers the flash point and has the benefit of increased safety during manufacture, storage and transport. It is also possible to disperse water-soluble components, such as water-soluble ionic surfactants, in advance in water and blend them into the composition of the present invention, particularly the aqueous phase.

In the cosmetic composition or the preparation for external use of the present invention, although the amount of water used is not limited, 0.1 to 4000 parts by mass, preferably 5 to 2000 parts by mass, of water can be mixed with 100 parts by mass of the total of the polymer(A), the solvent (B) and the oleophilic cosmetic raw material (C) in the composition containing each of the components. The resulting compositions can take the form of oil-in-water emulsions, water-in-oil emulsions, and the like, by using the surfactants described above.

[Other Component]

The cosmetic composition or the preparation for external use of the present invention may contain, as other optional components, various components used in cosmetics or external preparations, for example, a film-forming agent, a water-soluble polymer, an antibacterial preservative, and the like, in addition to the above components. In addition, in the cosmetic composition or the preparation for external use according to the present invention, at least one compound selected from the group consisting of amino acids or salts thereof, inorganic salts, and organic acids or salts thereof can be appropriately blended depending on the function of the cosmetic. Furthermore, the cosmetic composition or the preparation for external use of the present invention can be blended with each component usually blended in a cosmetic such as a pH adjusting agent, an antioxidant, a chelating agent, or the like, but is not particularly limited thereto. In addition, these components are used within a range that does not impair the object of the present invention.

[Film-Forming Agent]

The film-forming agent is a polymer component that forms a film-forming structure on the skin and hair. The copolymer (A) is a component which functions as a film-forming agent. Such film-forming agents include polymers selected from the following nonionic polymers, cationic polymers, anionic polymers, and amphoteric polymers; silicone resins, acrylic silicone resins, acrylic silicone dendrimer copolymers, polyamide modified silicones, alkyl modified silicone resin waxes, and the like, as described above. The selection method may be, for example, one or two more of the nonionic polymers, or two or more of the different polymers. These film-forming agents do not necessarily have to be water-soluble, but a water-soluble polymer used for the purpose of thickening or the like of a water-containing component and a part of the component overlap each other.

Suitable nonionic polymers include, for example, nonionic polymeric compounds such as polyvinyl pyrrolidone (Rubiscol K, manufactured by BASF), vinyl pyrrolidone/vinyl acetate copolymer (Rubiscol VA manufactured by BASF), vinyl pyrrolidone/dimethylaminoethyl methacrylate copolymer (Copolymer 937 manufactured by ISP), vinyl caprolactam/vinyl pyrrolidone/dimethylaminoethyl methacrylate copolymer (Copolymer VC713 manufactured by ISP), polyvinyl alcohol, polyoxypropylene butyl ether, and the like.

Suitable cationic polymers include, for example, cationic polymer compounds such as quaternary compounds of vinylpyrrolidone/dimethylaminoethylmethacrylate (GAFQUAT, manufactured by ISP), methylvinylimidazolidum chloride/vinylpyrrolidone copolymer (Rubicote, manufactured by BASF), cationized cellulose, cationized starch, cationized guar gum, vinylpyrrolidone/N, N-dimethylaminoethylmethacrylate copolymer diethylsulfate, and diallyl quaternary ammonium salt polymers, and the like.

Suitable anionic polymers include, for example, cationic polymer compounds such as acrylate/methacrylate ester copolymers (Plascize manufactured by Goo Chemical Co., Ltd.), vinyl acetate/crotonic acid copolymer (Resin 28-1310, manufactured by NSC Corporation), vinyl acetate/crotonic acid/vinyl neodecanate copolymer (Resin 28-2930 manufactured by NSC Corporation), methylvinylether/maleic acid half ester (GANTREZ ES manufactured by ISP), tert-butyl acrylate/ethyl acrylate/methacrylic acid copolymer (Luvimer manufactured by BASF), vinyl pyrrolidone/vinyl acetate/vinyl propionate copolymer (Luviskol VAP manufactured by BASF), vinyl acetate/crotonic acid copolymer (Luviset CA manufactured by BASF), vinyl acetate/crotonic acid/vinyl pyrrolidone copolymer (Luviset CAP manufactured by BASF), vinyl pyrrolidone/acrylate copolymer (Luviflex manufactured by BASF), acrylate/acrylamide copolymer (Ultrahold manufactured by BASF), vinyl acetate/butyl maleate/isobornyl acrylate copolymer (Advantage manufactured by ISP), acrylic alkanolamine, and urethane-modified acrylic polymer represented by WO 2005/054341 and WO 2008/004502, and the like.

Suitable amphoteric polymers include, for example, amphoteric acetates of dialkylaminoethylmethacrylate polymers (Yucaformer manufactured by Mitsubishi Chemical Corporation), octylacrylamide acrylate/hydroxypropyl acrylate/butylaminoethyl methacrylate copolymer (AMPHOMER manufactured by NSC Corporation), octyl acrylamide-butylaminoethyl methacrylate-hydroxypropyl methacrylate-acrylate copolymers, and the like.

As the alkyl-modified silicone resin wax, for example, silsesquioxane resin wax described in JP 2007-532754 T is preferable.

As acrylic silicone dendrimer copolymers, for example, vinyl polymers having carbosiloxane dendrimer structures at side chains as described in JP 4009382 B (JP 2000-063225 A), WO 2014/030771 (JP 5797618 B) are particularly preferred. Commercially available products include FA 4001 CM Silicone Acrylate, FA 4002 ID Silicone Acrylate manufactured by Dow Corning Toray Co., Ltd., and the like.

Examples of polyamide-modified silicones include siloxane-based polyamides described in, for example, U.S. Pat. No. 5,981,680, and commercially available products include 2-8178 Gellant and 2-8179 Gellant, and the like (manufactured by Dow Corning Corporation, USA).

As the alkyl-modified silicone wax, any wax-like alkyl-modified silicone at room temperature may be used, and include, for example, methyl-long-chain-alkyl polysiloxane capped at both ends of a molecular chain with trimethylsiloxy group, dimethyl polysiloxane/methyl-long-chain-alkylsiloxane copolymer capped at both ends of a molecular chain with trimethylsiloxy group, and long-chain-alkyl-modified dimethyl polysiloxane at both ends of a molecular chain, and the like. These commercially available products include AMS-C30 Cosmetic Wax, 2503 Cosmetic Wax and the like (manufactured by Dow Corning Corporation, USA).

[Water-Soluble Polymer]

The water-soluble polymer is blended for the purpose of improving the feeling of use of cosmetics, and any of amphoteric, cationic, anionic, nonionic, and water-swellable clay minerals can be used as long as it is used in ordinary cosmetic materials, and one or two or more types of water-soluble polymer can be used in combination. Since these water-soluble polymers have a thickening effect of the water-containing component, they are particularly useful for obtaining a water-containing cosmetics in the form of a gel, a water-in-oil cosmetic, a water-in-oil emulsion cosmetic, or an oil-in-water emulsion cosmetic.

[Antibacterial Preservative]

The cosmetic composition or the preparation for external use of the present invention preferably contains an antibacterial preservative from the viewpoint of preventing corruption and maintaining quality, for example, include paraoxybenzoic acid alkyl esters, benzoic acid, sodium benzoate, sorbic acid, potassium sorbate, and phenoxyethanol, and as antimicrobial agents, benzoic acid, salicylic acid, carbonic acid, sorbic acid, paraoxybenzoic acid alkyl esters, parachloromethacresol, hexachlorophene, benzalkonium chloride, chlorhexidine chloride, trichlorocarbanilide, triclosan, photosensitive, and the like are exemplified. Instead of using the preservative, the propagation of bacteria may be protected or prevented by using a pH adjusting agent, an antioxidant, a chelating agent, an organic acid, or the like.

[Dosages Form]

The cosmetic composition or the preparation for external use of the present invention may be in any form, such as liquid, emulsion, cream, solid, paste, gel, powder, multilayer, mousse, or spray.

As specific cosmetic products, the cosmetic composition or the preparation for external use of the present invention includes skin cosmetic materials such as skin cleaning products, skin care products, make-up products, antiperspirant products, and ultraviolet protection products; hair cosmetic materials such as hair washing agent products, hair dressing products, hair coloring products, hair grower products, hair-rinse products, hair conditioner products, and hair treatment products; bath cosmetic materials; hair growth agents, hair tonics, an analgesics, fungicides, anti-inflammatory agents, refreshers, and skin aging inhibitors, but is not limited hereto.

The skin cosmetic materials can be used on any part of the scalp, face (including lips, eyebrows, and cheeks), fingers, nails, and whole body. Specifically, skin cleaning products such as cleansing gels, cleansing creams, facial cleansing creams, eye make-up removers, facial cleansing foams, liquid soaps (body soaps), hand soaps, gelatinous soaps, shaving creams, removers, and anti-acne cosmetics; skin-care products such as skin creams, scalp treatments, skin milks, milk lotions, milky lotions, facial packs, body powder, essences, shaving lotions, and massage lotions; make-up products such as foundations, liquid foundations, oily foundations, make-up bases, cosmetic powders, face powders, blusher, lip creams, paste rouge, lip gloss, eye-creams, mascara, eyebrow pencil, and eyelash cosmetic materials; antiperspirants such as deodorants; and UV protection products such as sunscreens and sunburns (suntans) are exemplified.

Examples of the hair cosmetic materials include hair washing agents such as shampoos and rinse-in-shampoos; hair dressing products such as hair waxes, hair curl holding agents, setting agents, hair creams, hair sprays, and hair liquids; hair coloring products such as hair dyeing agents, hair color sprays, hair color rinses, and hair color sticks; hair grower agents such as hair tonics, hair treatment essences, and hair packs; hair-rinse or hair conditioning products such as oil rinses, cream rinses, treatment rinses, hair conditioners, and hair treatments. The bath cosmetic materials include a foam bath.

The form of the cosmetics according to the present invention is not particularly limited, and is preferably applicable to a liquid state, a W/O emulsion state, an O/W emulsion state, a W/O cream state, an O/W cream state, a solid state, a paste state, a gel state, a powder state, a multilayer state, a mousse state, a mist state, a granular state, a flake state, a crushed stone state, or the like. Particularly preferred forms are oil-in-water emulsions or water-in-oil emulsions, make-up cosmetics such as various foundations, liquid foundations, oily foundations, and ultraviolet protection products such as sunscreens, and dosage forms of these emulsion forms are particularly suitable from the viewpoint of film-forming performance of copolymer (A) and compatibility with various cosmetic raw materials.

[Cosmetic Raw Material Composition]

The copolymer (A) is preferably dispersed or dissolved in the solvent (B) and incorporated as a cosmetic raw material composition in a cosmetic material or an external preparation. In particular, a cosmetic raw material composition containing a copolymer (A) with a high hydroxyl group (OH) content in the molecule and a volatile solvent (B1) in which Si atoms bonded to the resin structure (A1) block constitute $RSiO_{3/2}$ units is excellent in affinity and compatibility with other cosmetic raw materials, is excellent in film-forming performance of the polymer (A), and a refreshed feel derived from the volatile solvent (B1) can be realized. The cosmetic raw material composition of the present invention may be in the form of a premix in which the above-mentioned cosmetic raw material substances (C) to (F) or other components are blended.

The content of the copolymer (A) in the cosmetic raw material composition of the present invention is not particularly limited, but is preferably 1 to 80 mass %, preferably 3 to 70 mass %, and preferably 5 to 60 mass %. If the content of the copolymer (A) is less than the above-mentioned lower limit, the amount of solvent may become excessive depending on the formulation, and the film-forming performance may become difficult to realize. On the other hand, when the content of the copolymer (A) exceeds the above upper limit, the liquid becomes viscous, and the handling workability at the time of blending may be lowered.

The cosmetic raw material composition of the present invention may contain an oleophilic cosmetic raw material (C), in particular, an organic ultraviolet protection component such as a cinnamic acid methyl ester, and is preferable from the viewpoint of improving the blending stability.

[Guidelines for Formulation Design and Expected Effects]

The cosmetic composition or the preparation for external use of the present invention is not particularly limited as to a formulation design thereof as long as it contains the copolymer (A) and other optional components depending on the purpose of the composition, but may be used in a manner to replace part or all of the formulation of a known cosmetic composition or preparation for external use, in particular, a formulation using a silicone-based film-forming agent, from the viewpoint of exploiting the film-forming property of the copolymer (A) and the affinity to other cosmetic raw materials. Specifically, in the formulation of cosmetics or external preparations disclosed in US 2007/0,196,309 A (Patent Document 1), WO 2014/151464 (Patent Document 2), U.S. Pat. No. 7,261,877 (Patent Document 3), JP 08-143426 A (Patent Document 4), JP 2000-063225 A, WO 2014/030771, U.S. Pat. No. 5,981,680, and the like, a silicone-based film-forming agent can be replaced with the present copolymer (A), and such is preferable. Furthermore, the copolymer (A) can replace part or all of the cosmetic or external preparation formulation containing the above-mentioned [Film-forming agent], which is well known, and is preferable. Formulations of such cosmetics or external preparations are encompassed within the scope of the present invention, and Applicants expect to clearly suggest such combinations or substitutions to a third party and obtain technical benefits in such formulations, including the technical effects described below.

Since the copolymer (A) has both a hard and less tackiness film-forming performance derived from the resin structure (A1) block and a flexibility derived from the linear structure (A2) block, it is possible to form a film-forming structure on skin or hair, which has less tackiness and is excellent in followability to the skin as compared with a conventionally known film-forming agent. Therefore, by replacing part or all of the formulation of cosmetics or external preparations containing the above-mentioned [Film-forming agent] with the present copolymer (A), improvement in feel, blending amount of active ingredient (e.g., content of ultraviolet protection ingredient), stability, and the like derived from the film are expected.

EXAMPLES

The cosmetic composition or the preparation for external use and the cosmetic raw material composition of the present invention will be explained in detail with reference to examples and comparative examples. In the formula, Me represents a methyl group and Et represents an ethyl group. In addition, unless otherwise specified, in the examples, the M unit is a siloxane unit represented by the $Me_3SiO_{1/2}$, the Q unit is a siloxane unit represented by the $SiO_{4/2}$, and the MQ resin means a resinous organopolysiloxane (resin) having a hydroxyl group bonded on the M unit, the Q unit, and silicon atoms of the Q unit. The average degree of polymerisation of the dimethylsiloxane units of polydimethylsiloxane was calculated from the ratio of the intensities of the peaks to the Si atoms constituting both ends by using $^{29}$Si-NMR. The weight-average molecular weight was determined as a value converted to standard polystyrene by GPC.

Synthesis Example 1: Copolymer a1

An equimolar mixture of 0.8 grams (3.53 mmol) of methyltriacetoxysilane and ethyltriacetoxysilane was added to a solution of 6 grams (1.68 mmol) of polydimethylsiloxane capped with silanol (—$SiMe_2(OH)$) groups at both ends (an average degree of polymerization of 48) and 10 grams of n-heptane, and stirred at room temperature for 30 minutes. As a result of $^{29}$Si-NMR analysis, it was found that the SiOH group disappeared completely and diacetoxysilylated. The solution was then added to a mixed solution of 34 grams of trimethyl siloxysilicate and 50 grams of n-heptane having a molar ratio of M units ($Me_3SiO_{1/2}$) to Q units ($SiO_{4/2}$) of 54:46, an OH group content derived from silanol groups of 3.13 wt %, a ratio of Q units bound to OH groups to total Q units of 26.5%, and a weight-average molecular weight of 2970, and heated and stirred for 2 hours while removing a by-product aqueous acetic acid aqueous solution by azeotropic dehydration. Water was added and heated to stir for 1 hour and allowed to stand to remove the lower layer. This operation was further repeated to completely remove the acetic acid. After azeotropic dehydration, the low boilers were removed by heating to give the MQ resin-polydimethylsiloxane copolymer <copolymer a1>.

The copolymer a1 is designed to have a mass ratio of MQ resin as a raw material and chain polydimethylsiloxane of 85:15, and contains T units represented by $MeSiO_{3/2}$ and $EtSiO_{3/2}$ which are bonded to Si atoms constituting a resin structure at a connecting site (Si—O—Si) of a resin structure and a linear structure by way of diacetoxysilylation in a condensation reaction.
Partial Structure of Copolymer a1:
MQ Resin Block (Si)—T Unit (Si)—O—(Si) Polydimethylsiloxane Block The residual OH group content in copolymer a1 was 2.28 mass %, the ratio of Q units bound to OH groups to total Q units was 20.5 mol %, and a weight-average molecular weight thereof was 18500.

Synthesis Example 2: Copolymer a2

An equimolar mixture of 1.07 grams (4.71 mmol) of methyltriacetoxysilane and ethyltriacetoxysilane was added to a solution of 8 grams (2.24 mmol) of polydimethylsiloxane capped with silanol (—$SiMe_2(OH)$) groups at both ends (an average degree of polymerization of 48) and 10 grams of n-heptane, and stirred at room temperature for 30 minutes. As a result of $^{29}$Si-NMR analysis, it was found that the SiOH group disappeared completely and diacetoxysilylated. The solution was then added to a mixed solution of 25.6 grams of trimethyl siloxysilicate having a molar ratio of M units ($Me_3SiO_{1/2}$) to Q units ($SiO_{4/2}$) of 54:46, an OH group content derived from silanol groups of 3.13 wt %, a ratio of Q units bound to OH groups to total Q units of 26.5%, and a weight-average molecular weight of 2970, 6.4 grams of trimethylsiloxysilicate having a molar ratio of M units ($Me_3SiO_{1/2}$) to Q units ($SiO_{4/2}$) of 51:49, an OH group content derived from silanol groups of 2.74 wt %, a ratio of Q units bound to OH groups to total Q units of 23.9%, and a weight-average molecular weight of 7400 and 50 grams of n-heptane, and heated and stirred for 2 hours while removing a by-product aqueous acetic acid aqueous solution by azeotropic dehydration. 5 grams of water was added and heated to stir for 1 hour and allowed to stand to remove the lower layer. This operation was repeated to completely remove the acetic acid. After azeotropic dehydration, the low boiling point substances were removed by heating to give the MQ resin-polydimethylsiloxane copolymer <copolymer a2>.

The copolymer a2 is designed to have a mass ratio of MQ resin as a raw material and chain polydimethylsiloxane of 80:20, and contains T units represented by $MeSiO_{3/2}$ or $EtSiO_{3/2}$ which are bonded to Si atoms constituting a resin structure at a connecting site (Si—O—Si) of a resin structure and a linear structure by way of diacetoxysilylation in a condensation reaction. Since methyltriacetoxysilane and ethyltriacetoxysilane used for diacetoxysilylation are equimolar, the ratio of the above-mentioned T units is 1:1.
Partial Structure of Copolymer a2:
MQ Resin Block (Si)—T Unit (Si)—O—(Si) Polydimethylsiloxane Block The residual OH group content in copolymer a2 was 2.07 mass %, the ratio of Q units bound to OH groups to total Q units was 19.3 mol %, and a weight-average molecular weight thereof was 28800.

Comparative Synthesis Example: Copolymer c without T Unit 1 gram of 28 wt % ammonia water was added to a mixture solution of 6 grams (1.68 mmol) of polydimethylsiloxane capped with silanol (—$SiMe_2(OH)$) groups at both ends (an average degree of polymerization of 48), 34 grams of trimethylsiloxysilicate having a molar ratio of M units ($Me_3SiO_{1/2}$) to Q units ($SiO_{4/2}$) of 54:46, an OH group content derived from silanol groups of 3.13 wt %, a ratio of Q units bound to OH groups to total Q units of 26.5%, and a weight-average molecular weight of 2970, and 60 grams of n-heptane, and heated and stirred at 40° C. for 6 hours. Then, the by-product water heated and stirred for 1 hour while removing a by-product water by azeotropic dehydration. The low boiling point substances were removed by heating to give the MQ resin-polydimethylsiloxane condensation product (copolymer c).

The copolymer c does not contain a component constituting a T unit, and has a partial structure in which a resin structure and a linear structure are simply bonded via a siloxane bond. The residual OH group content in copolymer c was 1.42 mass %, the ratio of Q units bound to OH groups to total Q units was 13.2 mol %, and a weight-average molecular weight thereof was 23200.

Example 1, 2 and Comparative Example 1, 2

The compositions according to the examples using the copolymer a1 and the copolymer a2 described above and the comparative examples using the copolymer c described above and conventional MQ silicone resins (MQ1600 manufactured by Dow Corning Corporation) were prepared and evaluated in the following manner.

Solubility evaluation: Polymers (the respective copolymers or MQ-silicone resins) and dimethylpolysiloxane (viscosity: 2 mPas·s, volatility) were dissolved beforehand in parts by mass shown in Table 1, and other components were added and stirred to confirm the appearance.

Film followability: A 20% dimethylpolysiloxane (viscosity: 2 mPas·s, volatility) solution of the respective polymers was applied to a commercially available latex film, and the solution was dried to form a film of about 50 μm on the latex film. Latex membranes were subsequently repeatedly stretched and the appearance of the films examined.

Tackiness: Solutions of 20% dimethylpolysiloxane (viscosities: 2 mPas s, volatility) of the respective polymers were coated on a glass plate, dried to form a film, and the tackiness was evaluated by contacting the glass plate.

Contact angle (water): 20% dimethylpolysiloxane (viscosities: 2 mPas·s, volatility) solutions of the respective polymers were coated on a glass plate, dried to form a film, and the contact angle of water was measured by an automated contact angle meter (manufactured by Kyowa Interface Science Co., Ltd).

Contact angle (artificial sebum): 20% dimethylpolysiloxane (viscosities: 2 mPas·s, volatility) solutions of the respective polymers were coated on a glass plate, dried to form a film, and the contact angle of artificial sebum was measured by an automated contact angle meter (manufactured by Kyowa Interface Science Co., Ltd).

In Examples 1, 2 and Comparative Example 1, copolymers prepared in Synthesis Examples 1 and 2 and Comparative Synthesis Examples, respectively, were blended. In Comparative Example 2, a MQ1600 manufactured by Dow Corning Corporation was blended.

TABLE 1

| | Experiment example | | | |
|---|---|---|---|---|
| | Example 1 | Example 2 | Comparative Example 1 | Comparative Example 2 |
| Polymer | 3 | 3 | 3 | 3 |
| Uvinul A | | 2 | | |
| Octyl methoxycinnamate | | 5 | | |
| Octocrylene | | 3 | | |
| Isotridecyl isononanoate | | 9 | | |
| Dimethyl polysiloxane (viscosity: 2 mPa · s) | | 12 | | |
| Solubility | Dissolution | Dissolution | Separated | Dissolution |
| Film followability | Not changed | Not changed | Not changed | Cracks |
| Tackiness | No cracks | No cracks | Cracks generated | Cracks generated |

TABLE 1-continued

| | Experiment example | | | |
|---|---|---|---|---|
| | Example 1 | Example 2 | Comparative Example 1 | Comparative Example 2 |
| Contact angle (water) | 102 | 100 | 101 | 96 |
| Contact angle (artificial sebum) | 57 | 49 | 61 | 31 |

As described in the above examples, the copolymers a1 and a2 having T units were uniformly dissolved with other cosmetic raw material components, were excellent in the feeling of use, and were able to realize a film-forming property having a high skin followability. On the other hand, in the copolymer c obtained in the comparative synthesis example, the other cosmetic raw material components were separated, and not only the blending stability was inferior, but also only a solid adhesive film was obtained. In addition, in the evaluations using MQ1600, since it was a hard film derived from a resin, there was no skin followability, resulting in cracks. In addition, the contact angle evaluation of the Examples was comparable and equivalent to that of the Comparative Examples in both water and artificial sebum. From the above, it is possible to confirm the usefulness of a cosmetic composition or a preparation for external use containing a cosmetic material (film-forming agent) excellent in blending stability, feeling of use, and skin followability by using the copolymers a1 and a2 of the present invention, unlike the conventionally known film-forming agents.

Formulation Examples 1 to 11

Formulations of the cosmetic composition or the preparation for external use according to the present invention are shown below using the copolymer compositions using the copolymers a1 and a2 obtained in Synthesis Example 1 and Synthesis Example 2.

In the respective formulation examples, "copolymer composition described in Synthesis Example X" refers to a 20% dimethylpolysiloxane (viscosity: 2 mPas·s, volatility) solution of Copolymer a1 (Synthesis Example 1) or Copolymer a2 (Synthesis Example 2), and "parts" are all parts by mass.

[Formulation Example 1] Liquid Foundation (W/O)

| (Component) | |
|---|---|
| 1. Decamethyl cyclopentasiloxane | 30 parts |
| 2. Isotridecyl isononanoate | 3 parts |
| 3. Glyceryl tricaprylcaprate | 2 parts |
| 4. Polyether-modified silicone (Note 1) | 1.5 parts |
| 5. Diglycerin-modified silicone (Note 2) | 0.5 parts |
| 6. Organo-modified clay minerals (Benton 38V) | 1.5 parts |
| 7. Octyl methoxycinnamate | 5 parts |
| 8. Silicone-treated titanium oxide | 8.5 parts |
| 9. Silicone-treated red iron oxide | 0.4 part |
| 10. Silicone-treated yellow iron oxide | 1 part |
| 11. Silicone-treated black iron oxide | 0.1 part |
| 12. Decamethyl cyclopentasiloxane, Dimethicone crosspolymer (Note 3) | 2 parts |
| 13. Copolymer composition described in Synthesis Example 1 | 2 parts |
| 14. 1,3-butylene glycol | 5 parts |
| 15. Glycerin | 3 parts |
| 16. Sodium chloride | 0.5 part |

-continued

| (Component) | | |
|---|---|---|
| 17. Preservative | q.s. | |
| 18. Purified water | balance | |
| 19. Perfume | q.s. | |

(Note 1)
ES-5300 (manufactured by Dow Corning Toray Co., Ltd.) was used.
(Note 2)
DC9040 (manufactured by Dow Corning Corporation) was used.
(Note 3)
ES-5600 (manufacured by Dow Corning Toray Co., Ltd.) was used.

(Manufacturing Method)

Step 1: Components 1, 4, 6, 7, 12, and 13 were stirred and mixed.

Step 2: Components 2, 3, 5, and 8 to 11 were kneaded and mixed using three rolls.

Step 3: Under stirring, the mixture of Step 2 was added to the mixture obtained in Step 1, followed by stirring and mixing.

Step 4: The aqueous phase in which the components 14 to 19 were uniformly dissolved was added to the mixture obtained in Step 3 and emulsified, and the mixture was filled in a container to obtain a product.

The obtained W/O type liquid foundation was excellent in emulsification stability, was excellent in water resistance and cosmetic durability, was hardly noticeable in texture and wrinkles, and was excellent in elongation and stickiness at the time of use.

[Formulation Example 2] Liquid Foundation (W/O)

| (Component) | |
|---|---|
| 1. Isododecane | 20 parts |
| 2. Isohexadecane | 10 parts |
| 3. Isotridecyl isononanoate | 3 parts |
| 4. Glyceryl tricaprylcaprate | 2 parts |
| 5. Polyether-modified silicone (Note 1) | 1.5 parts |
| 6. Glycerin co-modified organopolysiloxane B | 0.5 part |
| 7. Organo-modified clay minerals (Benton 38V) | 1.5 parts |
| 8. Octyl methoxycinnamate | 5 parts |
| 9. Octylsilane treated titanium oxide | 8.5 parts |
| 10. Octylsilane treated red iron oxide | 0.4 part |
| 11. Octylsilane treated yellow iron oxide | 1 part |
| 12. Octylsilane treated black iron oxide | 0.1 part |
| 13. Dimethicone, Dimethicone crosspolymer (Note 2) | 2 parts |
| 14. Copolymer composition described in Synthesis Example 2 | 1 part |
| 15. Trimethylsiloxysilicate | 0.5 part |
| 16. 1,3-butylene glycol | 5 parts |
| 17. Glycerin | 3 parts |
| 18. Sodium chloride | 0.5 parts |
| 19. Preservative | q.s. |
| 20. Purified water | balance |
| 21. Perfume | q.s. |

(Note 1)
ES-5300 (manufactured by Dow Corning Toray Co., Ltd.) was used.
(Note 2)
DC9045 (manufactured by Dow Corning Corporation) was used.

(Manufacturing Method)

Step 1: Components 1, 2, 5, 7, 8, 13, 14, and 15 were stirred and mixed.

Step 2: Components 3, 4, 6, and 9 to 12 were kneaded and mixed using three rolls.

Step 3: Under stirring, the mixture of Step 2 was added to the mixture obtained in Step 1, followed by stirring and mixing.

Step 4: The aqueous phase in which the components 16 to 21 were uniformly dissolved was added to the mixture obtained in Step 3 and emulsified, and the mixture was filled in a container to obtain a product.

The obtained W/O type liquid foundation was excellent in emulsification stability, was excellent in water resistance and cosmetic durability, was hardly conspicuous in texture and wrinkles, had a light feel, and was excellent in adhesiveness at the time of use.

[Formulation Example 3] Liquid Foundation (O/W)

| (Component) | |
|---|---|
| 1. Carboxydecyl trisiloxane | 1 part |
| 2. Polysorbate 80 | 1.2 parts |
| 3. Sorbitan sesquioleate | 0.2 part |
| 4. Glyceryl stearate | 1.5 parts |
| 5. Behenyl alcohol | 2.5 parts |
| 6. Cyclopentasiloxane | 8 parts |
| 7. Dimethicone (viscosity: 6 mPa · s) | 3 parts |
| 8. Squalane | 3 parts |
| 9. Isotridecyl isononanoate | 3 parts |
| 10. Glyceryl tricaprylcaprate | 3 parts |
| 11. Copolymer composition described in Synthesis Example 1 | 1 part |
| 12. Glycerin co-modified organopolysiloxane (Note 1) | 0.2 part |
| 13. Silicone-treated titanium oxide | 8.5 parts |
| 14. Silicone-treated red iron oxide | 0.4 part |
| 15. Silicone-treated yellow iron oxide | 1 part |
| 16. Silicone-treated black iron oxide | 0.1 part |
| 17. 1,3-butylene glycol | 8 parts |
| 18. Sodium hydroxide solution (1%) | 15 parts |
| 19. Carbomer (2%) | 10 parts |
| 20. Purified water | balance |

(Note 1)
ES-5600 (manufactured by Dow Corning Toray Co., Ltd.) was used.

(Manufacturing Method)

Steps 1: 1 to 8 and 11 were mixed by heating and stirring.

Step 2: 9, 10 and 12 to 16 were kneaded and mixed using three rolls.

Step 3: Under stirring, the mixture of Step 2 was added to the mixture obtained in Step 1, followed by stirring and mixing.

Step 4: An aqueous phase in which the components 17 to 18 and 20 were uniformly dissolved was added to the mixture obtained in Step 3 at 70° C. and emulsified, 19 was added with stirring, and cooled to be filled in a container to obtain a product.

The obtained O/W type liquid foundation was excellent in emulsification stability, was excellent in water resistance and cosmetic durability, was hardly conspicuous in texture and wrinkles, and was excellent in elongation and stickiness at the time of use.

[Formulation 4] Sunscreen (W/O)

| (Component) | |
|---|---|
| 1. Dimethicone (viscosity: 6 mPa · s) | 3.8 parts |
| 2. Cyclopentasiloxane | 6.7 parts |
| 3. Isotridecyl isononanoate | 4 parts |
| 4. Polyether-modified silicone (Note 1) | 2 parts |
| 5. Cyclopentasiloxane, Cross-linked polyether-modified silicone (Note 2) | 2.5 parts |
| 6. Cyclopentasiloxane, Dimethicone crosspolymer (Note 3) | 1.5 parts |

-continued

| (Component) | |
|---|---|
| 7. Organo-modified bentonite | 0.2 part |
| 8. Silicone-treated fine particulate zinc oxide dispersion (zinc oxide 60 wt %) (Note 4) | 35 parts |
| 9. Silicone-treated fine particulate titanium oxide dispersion (titanium oxide 40 wt %) (Note 5) | 25 parts |
| 10. Copolymer composition described in Synthesis Example 2 | 3.3 parts |
| 11. 1,3-butylene glycol | 2 parts |
| 12. Sodium citrate | 0.2 part |
| 13. Sodium chloride | 0.5 part |
| 14. Purified water | balance |

(Note 1)
ES-5300 (manufactured by Dow Corning Toray Co., Ltd.) was used.
(Note 2)
DC-9011 (manufactured by Dow Corning Toray Co., Ltd.) was used.
(Note 3)
DC-9040 (manufactured by Dow Corning Toray Co., Ltd.) was used.
(Note 4)
10 parts of ES-5600 (manufactured by Dow Corning Toray Co., Ltd.), 40 parts of fine particulate titanium oxide (trade name: MTY-02, manufactured by Tayca Corporation, particle diameter: 10 nm) and 50 parts of decamethyl pentasiloxane were mixed with zirconia beads, and those slurry dispersed with a paint shaker was used.
(Note 5)
5 parts of ES-5600 (manufactured by Dow Corning Toray Co., Ltd.), 60 parts of fine particulate zinc oxide (trade name: FINEX-30S-LPT, manufactured by Sakai Chemical Industry Co., Ltd., particle diameter: 35 nm) and 35 parts of decamethyl pentasiloxane were mixed with zirconia beads, and those slurry dispersed with a paint shaker was used.

(Manufacturing Method)
Step 1: Components 1 to 10 are mixed.
Step 2: Components 11 to 14 are mixed.
Step 3: The aqueous phase obtained in Step 2 was added to the mixture obtained in Step 1 under stirring, emulsified, and then filled in a container to obtain a product.

The obtained sunscreen could be stocked for a long time at around 40° C. (summer temperature) without causing separation of oily components and powders, and was excellent in time stability. In addition, when used, it had an excellent feeling of use with good elongation and spreading, had reduced tackiness, was free from irritation, and provided a sustained ultraviolet protection effect. Such a good sense of use was not changed even before and after storage at about 40° C.

[Formulation Example 5] Sunscreen (Shaking Type)

| (Component) | |
|---|---|
| 1. Octyl methoxycinnamate | 6 parts |
| 2. Isotridecyl isononanoate | 7 parts |
| 3. Polyether-modified silicone (Note 1) | 3 parts |
| 4. Diethylamino hydroxybenzoyl hexyl benzoate | 2 parts |
| 5. Titanium oxide slurry (Note 1) | 5 parts |
| 6. Zinc oxide slurry (Note 2) | 28 parts |
| 7. Cyclopentasiloxane | 18.2 parts |
| 8. Dimethicone crosspolymer | 3 parts |
| 9. Trimethylsiloxysilicate | 2 parts |
| 10. Copolymer composition described in Synthesis Example 1 | 1 part |
| 11. Preservative | 0.1 part |
| 12. Ethanol | 5 parts |
| 13. 1,3-butylene glycol | 3 parts |
| 14. Purified water | balance |

(Note 1)
ES-5300 (manufactured by Dow Corning Toray Co., Ltd.) was used.
(Note 2)
Fine particulate titanium oxide described in Formulation Example 4 was used.
(Note 3)
Fine particulate zinc oxide described in Formulation Example 4 was used.

(Manufacturing Method)
Step 1: Components 1 to 10 are mixed.
Step 2: A mixture of components 11 to 14 is added to the mixture of Step 1 and the mixture is emulsified.

The resulting sunscreen had a reduced tackiness and was excellent feel of use when applied on the skin and provided a sustained UV protection effect.

[Formulation Example 6] Foundation Cream

| (Component) | |
|---|---|
| 1. Dimethyl polysiloxane (viscosity: 2 mPa · s) | 2 parts |
| 2. Decamethyl cyclopentasiloxane | 10 parts |
| 3. Polyether-modified silicone (Note 1) | 2.5 parts |
| 4. Cetyl isooctanoate | 5 parts |
| 5. Diglycerin-modified silicone (Note 2) | 0.5 part |
| 6. Copolymer composition described in Synthesis Example 2 | 3 part |
| 7. 2-ethylhexyl paramethoxycinnamate | 2 parts |
| 8. Silicone elastomer (Note 3) | 4 parts |
| 9. Silicone-treated titanium oxide | 6 parts |
| 10. Silicone-treated red iron oxide | 0.3 part |
| 11. Silicone-treated yellow iron oxide | 0.7 part |
| 12. Silicone-treated black iron oxide | 0.07 part |
| 13. Organo-modified bentonite | 0.5 part |
| 14. Barium sulfate | 2 parts |
| 15. Talc | 1 part |
| 16. Nylon powder | 3 parts |
| 17. Preservative | q.s. |
| 18. Xanthan gum | 0.1 part |
| 19. L-ascorbic acid phosphate ester magnesium | 0.3 part |
| 20. Purified water | balance |

(Note 1)
ES-5612 (manufactured by Dow Corning Toray Co., Ltd.) was used.
(Note 2)
ES-5600 (manufactured by Dow Corning Toray Co., Ltd.) was used.
(Note 3)
9045 Silicone Elastomer Blend (manufactured by Dow Corning Corporation) was used.

(Manufacturing Method)
Step 1: Components 1 to 16 are mixed and dispersed.
Step 2: Components 17 to 20 are mixed.
Step 3: To the mixture obtained in Step 1, the mixture obtained in Step 2 was added and emulsified at room temperature, and the mixture was filled in a container to obtain a product.

The foundation cream was excellent in elongation and spreading, and was excellent in uniformity of the decorative film and adhesion to the skin. In addition, texture, wrinkles, and pore conspicuousness were less prominent. The foundation cream had a stable emulsified state.

[Formulation Example 7] Hair Mist

| (Component) | |
|---|---|
| 1. Purified water | balance |
| 2. Betaine | 0.6 part |
| 3. Creatine | 0.2 part |
| 4. Hydroxyethyl urea | 1 part |
| 5. Ethyl lactate | 0.1 part |
| 6. Butylene glycol | 5 parts |
| 7. Methylparaben | 0.15 part |
| 8. Alcohol | 15 parts |
| 9. PEG/PPG-30/10 dimethicone/dipropylene glycol | 1 part (Note 1) |
| 10. Glycereth-25 PCA isostearate | 0.5 part |
| 11. Bis-isobutyl PEG-14/amodimethicone copolymer | 1 part (Note 2) |
| 12. Bis-ethoxydiglycol cyclohexane dicarboxylate | 2 parts |
| 13. Copolymer composition described in Synthesis | 5 part |

Example 2

(Note 1)
BY25-339 (manufactured by Dow Corning Corporation) was used.
(Note 2)
AP-8201 (manufactured by Dow Corning Corporation) was used.

(Manufacturing Method)

Step 1: Components 1 to 7 are mixed and dispersed.

Step 2: Components 8 to 13 are mixed.

Step 3: To the mixture obtained in Step 1, the mixture obtained in Step 2 was added and emulsified at room temperature, and the mixture was filled in a container to obtain a product.

[Formulation Example 8] Hair Cream

| | | |
|---|---|---|
| 1. | Ethanol/PEG/PPG-30/10 dimethicone PEG12 dimethicone Phenyl trimethicone dipropylene glycol (Note 1) | 7 parts |
| 2. | Aminopropyl trimethicone (Note 2) | 2 parts |
| 3. | Phenyl trimethicone (Note 3) | 2 parts |
| 4. | Caprylyl trimethicone (Note 4) | 1 part |
| 5. | Dimethicone (Note 5) | 2 parts |
| 6. | Dimethicone (Note 6) | 4 parts |
| 7. | Copolymer of Synthesis Example 1 | 1 part |
| 8. | 2-Cetyl ethylhexanoate | 1.2 parts |
| 9. | Purified water | balance |
| 10. | Disodium hydrogen phosphate | 0.02 part |
| 11. | Sodium phosphate | 0.01 part |
| 12. | Polydecaglyceryl-10 Eicosanedioate/Tetradecanoic acid | 2 parts |
| 13. | Inositol | 2 parts |
| 14. | Ethyl lactate | 0.1 part |
| 15. | Hydroxyethyl urea | 2.8 parts |
| 16. | Preservative | 0.1 part |
| 17. | Carbomer (Note 7) | 0.32 part |
| 18. | Purified water | 20.18 parts |
| 19. | Hydroxypropyl starch phosphate | 0.5 part |
| 20. | Alcohol | 7 parts |
| 21. | Triethanolamine | 0.6 part |

(Note 1)
FB-2540 Emulsifier Blend (manufactured by Dow Corning Corporation) was used.
(Note 2)
2-2078 (manufactured by Dow Corning Corporation) was used.
(Note 3)
556 Cosmetic fluid (manufactured by Dow Corning Corporation) was used.
(Note 4)
FZ-3196 (manufactured by Dow Corning Corporation) was used.
(Note 5)
XIAMETER PMX-200 Silicone Fluid 1.5CS was used.
(Note 6)
XIAMETER PMX-200 Silicone Fluid 350CS was used.
(Note 7)
Carbopol 980 was used.

(Manufacturing Method)

Step 1: Components 1 to 8 are mixed and dispersed.

Step 2: Components 8 to 13 are mixed.

Step 3: Components 14 to 19 are mixed at 50° C.

Step 4: Components 20 and 21 are mixed.

Step 5: Mix steps 2 and 3.

Step 6: Add Step 1 to Step 5 and emulsify.

Step 7: Add Step 4.

[Formulation Example 9] Rinse-Off Conditioner

| | | |
|---|---|---|
| 1. | Hydroethylcellulose | 1.5 parts |
| 2. | Purified water | balance |
| 3. | Dimethicone, Dimethicone/vinyl dimethicone crosspolymer | 3.0 parts |
| 4. | Dimethicone | 3.0 parts |
| 5. | Copolymer of Synthesis Example | 1 part |
| 6. | Cetrimonium chloride | 0.3 part |
| 7. | Cetostearyl alcohol | 1.0 part |
| 8. | Pituitous Fluid (Note 1) | 3.0 parts |
| 9. | Phenoxyethanol | 0.2 part |

(Note 1)
3901 Liquid Satin Blend (manufactured by Dow Corning Corporation) was used.

(Manufacturing Method)
1. Purified water is heated to 80° C.
2. 1 was added to the component of Step 1 and dispersed.
3. Components 3 to 5 are dispersed.
4. Components 6 to 8 are dispersed.
5. The mixture of Step 2 and the mixture of Step 4 are dispersed and the mixture of Step 3 is added thereto.
6. The obtained mixture is cooled to 40° C. and Component 9 is added thereto.

[Formulation Example 10] Lip Gloss

| | | |
|---|---|---|
| 1. | Dimer dilinoleyl hydrogenated rosin condensation product | 5.0 parts |
| 2. | Dimer dilinoleyl diisostearate | 10.0 parts |
| 3. | Isotridecyl isononanoate | 10.0 parts |
| 4. | SH 556 Fluid | 5.0 parts |
| 5. | Copolymer of Synthesis Example 1 | 1 part |
| 6. | Hydrogenated polyisobutene | 35.5 parts |
| 7. | Hydrogenated polystyrene/Isoprene polymers, Hydrogenated polydecene | 30.0 parts |
| 8. | Polyether-modified silicone (Note 1) | 3.5 parts |

(Manufacturing Method)

Components 1 to 8 were mixed, and the mixture was filled in a container to obtain a lip gloss.

[Formulation Example 11] Lipstick

| (Component) | | |
|---|---|---|
| 1. | Triethylhexanoin | 10.0 parts |
| 2. | Cetyl ethylhexanoate | 17.0 parts |
| 3. | Sorbitan sesquiisostearate | 4.0 part |
| 4. | Microcrystalline wax | 10.0 parts |
| 5. | Paraffin wax | 15.0 parts |
| 6. | Diisostearyl malate | 7.0 parts |
| 7. | Glyceryl triisostearate | 9.0 parts |
| 8. | Propylene glycol dicaprate | 7.0 parts |
| 9. | Stearoyl Inulin (Product name: Rheopearl ISL2 manufactured by Chiba Flour Milling Co., Ltd.) | 2.0 parts |
| 10. | Co-modified organopolysiloxane P7 | 3.0 parts |
| 11. | Isododecane/(Acrylates/Polytrimethylsiloxymethacrylate) Copolymer (Note 1) | 3.0 parts |
| 12. | Copolymer of Synthesis Example 1 | 2.0 parts |
| 13. | Yellow No. 4 | q.s. |
| 14. | Titanium oxide | 1.0 part |
| 15. | Black iron oxide | 1.0 part |
| 16. | Mica | 1.0 part |
| 17. | Red No. 104 | q.s. |
| 18. | Purified water | 7.0 parts |
| 19. | 1,3-butylene glycol | 1.0 part |
| 20. | Preservative | q.s. |
| 21. | Perfume | q.s. |

(Note 1)
FA-4002ID (manufactured by Dow Corning Toray Co., Ltd.) was used.

(Manufacturing Method)

Step 1: Components 1 to 17 are heated and dissolved.

Step 2: Components 18 to 20 are mixed.

Step 3: The mixture of Step 2 is added to the mixture of Step 1, and further stirred and mixed.

Step 4: Component 21 was added to the mixture of Step 3, and the mixture was filled in a container to obtain a product.

INDUSTRIAL APPLICABILITY

Since the resin-linear organopolysiloxane block copolymer obtained by the synthetic example of the present invention is excellent in film forming property, it is possible to protect various tissues such as hair, skin, and skin surfaces and to carry various active ingredients on various tissues by incorporating the resin-linear organopolysiloxane block copolymer into a cosmetic agent, a topical agent, or a medical composition other than the formulations shown here, making use of the film forming property, and forming a film on the human body. In particular, since the copolymer has flexibility and compliance derived from a linear structure, the copolymer has flexibility while being a hard and strong coating derived from a resin. Therefore, it may be used as a cosmetic composition or a topical composition according to the present invention in a form in which a package or a capsule is formed by coating an active ingredient. The copolymer is used for other purposes, various external preparations, paints, coating agents, antifoaming agents, deodorants, and the like, and can be incorporated into products other than cosmetics.

The invention claimed is:

1. A cosmetic composition or a preparation for external use, comprising:
   a resin-linear organopolysiloxane block copolymer (A) having a structure in which a resin structure (A1) block having a siloxane unit represented by $R^1SiO_{3/2}$ or by $SiO_{4/2}$ where $R^1$ is a monovalent organic group, a hydroxyl group or an alkoxy group having 1 to 6 carbon atoms and a linear structure (A2) block represented by $(R_2SiO_{2/2})_n$ where n is a number of 5 or more, and R is an alkyl group, a fluoroalkyl group, or an aryl group are connected by a Si—O—Si bond, wherein one of the Si atoms of the Si—O—Si bond is present in an $RSiO_{3/2}$ unit.

2. The cosmetic composition or the preparation for external use according to claim 1, wherein the resin-linear organopolysiloxane block copolymer (A) contains $PhSiO_{3/2}$ units where Ph is a phenyl group or $R^2SiO_{3/2}$ units where $R^2$ is an alkyl group having 3 to 20 carbon atoms.

3. The cosmetic composition or the preparation for external use according to claim 1, wherein the resin-linear organopolysiloxane block copolymer (A) contains $R^4R^5R^6SiO_{1/2}$ units where $R^4$ to $R^6$ are each independently monovalent organic groups and at least two of them are aryl groups.

4. The cosmetic composition or the preparation for external use according to claim 1, wherein the resin-linear organopolysiloxane block copolymer (A) has a hydroxyl group (OH) content in the molecule of 1.50 mass % or more.

5. The cosmetic composition or the preparation for external use according to claim 1, wherein the resin-linear organopolysiloxane block copolymer (A) has $SiO_{4/2}$ units and 15 mol % or more of all $SiO_{4/2}$ units have hydroxyl groups on Si atoms.

6. The cosmetic composition or the preparation for external use according to claim 1, further comprising a solvent (B) of the resin-linear organopolysiloxane block copolymer (A).

7. The cosmetic composition or the preparation for external use according to claim 6, wherein the resin-linear organopolysiloxane block copolymer (A) and the solvent (B) thereof have solubility in methyl cinnamate ester.

8. The cosmetic composition or the preparation for external use according to claim 6, wherein the solvent (B) is a volatile solvent (B1).

9. The cosmetic composition or the preparation for external use according to claim 1, further comprising an oleophilic cosmetic raw material (C).

10. The cosmetic composition or the preparation for external use according to claim 1, further comprising a surfactant (D).

11. The cosmetic composition or the preparation for external use according to claim 1, further comprising a powder or colorant (E).

12. The cosmetic composition or the preparation for external use according to claim 1, further comprising an alcohol (F).

13. The cosmetic composition or the preparation for external use according to claim 1, which is in a form of an oil-in-water emulsion or a water-in-oil emulsion.

14. A cosmetic raw material composition comprising:
    a resin-linear organopolysiloxane block copolymer (A) having a structure in which a resin structure (A1) block having a siloxane unit represented by $R^1SiO_{3/2}$ or by $SiO_{4/2}$ where $R^1$ is a monovalent organic group, a hydroxyl group or an alkoxy group having 1 to 6 carbon atoms and a linear structure (A2) block represented by $(R_2SiO_{2/2})_n$ where n is a number of 5 or more are connected by a Si—O—Si bond, wherein one of the Si atoms of the Si—O—Si bond is present in an $RSiO_{3/2}$ unit; and
    a volatile solvent (B 1).

* * * * *